(12) United States Patent
Bittner et al.

(10) Patent No.: US 9,180,136 B2
(45) Date of Patent: Nov. 10, 2015

(54) IDENTIFICATION AND TREATMENT OF CANCER SUBSETS

(75) Inventors: Michael Bittner, Phoenix, AZ (US); Jeffrey M. Trent, Paradise Valley, AZ (US); Aleksandar Sekulic, Scottsdale, AZ (US); Mohammad R. Abbaszadegan, Tempe, AZ (US)

(73) Assignees: The Translational Genomics Research Institute, Phoenix, AZ (US); Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/274,058

(22) Filed: Oct. 14, 2011

(65) Prior Publication Data

US 2012/0264720 A1 Oct. 18, 2012

Related U.S. Application Data

(60) Provisional application No. 61/393,065, filed on Oct. 14, 2010.

(51) Int. Cl.

| A61K 31/6615 | (2006.01) |
| C12Q 1/68 | (2006.01) |
| G01N 21/64 | (2006.01) |
| C40B 30/04 | (2006.01) |
| G01N 33/573 | (2006.01) |
| C40B 40/06 | (2006.01) |
| A61P 35/00 | (2006.01) |
| G01N 33/574 | (2006.01) |

(52) U.S. Cl.
CPC .......... *A61K 31/6615* (2013.01); *C12Q 1/6886* (2013.01); *G01N 33/57492* (2013.01); *C12Q 2600/106* (2013.01); *C12Q 2600/118* (2013.01); *C12Q 2600/158* (2013.01)

(58) Field of Classification Search
CPC ............. A61K 31/6615; C12Q 1/6886; C12Q 2600/106; C12Q 2600/118; C12Q 2600/158; G01N 33/57492
See application file for complete search history.

(56) References Cited

PUBLICATIONS

Aleksandar Sekulic, Loss of Inositol Polyphosphate 5-Phosphatase is an Early Event in development of Cutaneous Squamous Cell Carcinoma, Cancer Prevention Research, 2010:3:1277-1283.*
Ivana Vucenik, Cancer Inhibition by Inositol Hexaphosphate (IP6) and Inositol:From Laboratory to Clinic, The Journal of Nutrition, 133:pp. 3778-3784.*
Florence De Smedt, Cloning and Expression of human brain type I inositol 1,4,5-trisphosphate 5-phosphatase, FEBS Letters, 347, 1994, pp. 69-72.*
Seth C. Janus, Inositol Hexaphosphate and Paclitaxel:Symbiotic Treatment of Oral Cavity Squamous Cell Carcinoma, Laryngoscope, 117, 2007, pp. 1381-1388.*
MedlinePlus Medical Dictionary, Defintion of "Metabolite". Accessed Apr. 24, 2013.*
Answers.com, Definition of "metabolite". Accessed Aug. 23, 2010.*
Rakesh K. Jain, Barriers to Drug Delivery in Solid Tumors, Scientific American, Jul. 1994, 271(1) pp. 58-65.*
Trisha Gura, Systems for Identifying New Drugs Are Often Faulty, Science, 1997, vol. 278 No. 5340 pp. 1041-1042.*
UniProt Protein Database, Accession Q14642, Human INPP5A, pp. 1-7, accessed on Jul. 8, 2014.*
GenBank Database, GenBank:Hl140155.1, pp. 1-2, accessed on Jul. 8, 2014.*

* cited by examiner

*Primary Examiner* — James H Alstrum Acevedo
*Assistant Examiner* — Erinne Dabkowski

(57) ABSTRACT

The present invention relates to methods of selectively treating a patient with skin squamous cell carcinoma are disclosed. Specifically, the methods comprise assessing whether or not the tumor will be responsive to IP6 treatment by using reduced INPP5A expression level as an indicator. The present invention further provides methods of assessing the progression of the disease, and kits that facilitate these methods as disclosed.

7 Claims, 18 Drawing Sheets
(8 of 18 Drawing Sheet(s) Filed in Color)

A  B

```
                       SEQUENCE LISTING

<160> NUMBER OF SEQ ID NOS: 6

<210> SEQ ID NO 1
<211> LENGTH: 2938
<212> TYPE: DNA
<213> ORGANISM: Homo sapiens
<220> FEATURE:
<221> NAME/KEY: misc_feature
<223> OTHER INFORMATION: INPP5A mRNA/cDNA NCBI Reference Sequence
      NM_005539.3

<400> SEQUENCE: 1
gcgcgggccg ctgtgaggcg cggcggcgag cgacgggcgc ggggccgcgg agcagcgagc    60
gagcgagcga gcgcgaggcc ggagcccgg ccaggcccgg ccgacccgcc gagcccgcga   120
tgcgccccgg ggccgccccc cggcgcagct gacgccccgc ggccccgcga agaccccggc   180
cggccggtcc cggaggaagc ggccgccgcc gccgccgccc agcccagcgc ccgcgccgcc   240
cgggcaccat ggcggggaag gcggccgccc cgggcaccgc ggtgctgctg gtcacggcca   300
acgtgggctc gctcttcgac gacccagaaa acctgcagaa gaactggctt cgggaatttt   360
accaggtcgt gcacacacac aagccgcact tcatggcctt gcactgtcag gagtttggag   420
ggaagaacta cgaggcctcc atgtcccacg tggacaagtt cgtcaaagaa ctattgtcga   480
gtgatgcgat gaaagaatat aacagggctc gagtctacct ggatgaaaac tacaaatccc   540
aggagcactt cacggcacta ggaagctttt attttcttca tgagtcctta aaaaacatct   600
accagtttga ctttaaagct aagaagtata gaaaggtcgc tggcaaagag atctactcgg   660
ataccttaga gagcacgccc atgctggaga aggagaagtt tccgcaggac tacttccccg   720
agtgcaaatg gtcaagaaaa ggcttcatcc ggacgaggtg gtgcattgca gactgtgcct   780
ttgacttggt gaatatccat cttttccatg atgcttccaa tctggtcgcc tgggaaacaa   840
gcccttccgt gtactcggga atccggcaca aggcactggg ctacgtgctg gacagaatca   900
ttgatcagcg attcgagaag gtttcctact ttgtatttgg tgatttcaac ttccggctgg   960
attccaagtc cgtcgtggag acgctctgca caaaagccac catgcagacg gtccgggccg  1020
ccgacaccaa tgaagtggtg aagctcatat ttcgtgagtc ggacaacgac cggaaggtta  1080
tgctccagtt agaaaagaaa ctcttcgact acttcaacca ggaggttttc cgagacaaca  1140
acggcaccgc gctcttggag tttgacaagg agttgtctgt ctttaaggac agactgtatg  1200
aactggacat ctcgttccct cccagctacc cgtacagtga ggacgcccgc cagggtgagc  1260
agtacatgaa caccggtgc ccagcctggt gtgaccgcat cctcatgtcc ccgtctgcca  1320
aggagctggt gctgcggtcg gagagcgagg agaaggttgt cacctatgac cacattgggc  1380
ccaacgtctg catgggagac cacaagcccg tgttcctggc cttccgaatc atgcccgggg  1440
```

```
caggtaaacc tcatgcccat gtgcacaagt gttgtgtcgt gcagtgacgt ggtgggaaga    1500
gatgccagcg ccacgagagg acacttcgtg agcctccctg tagccgtgga ccgaatacgc    1560
actcttgaaa gctgcatcga gaacccgccc aagcgccacc tgctagacgg ccagccccac    1620
acttcgcttc agcctccgga ccattccgga gcagcctcac atacctcact gtctcgtctg    1680
tctatgtgac attaagtaga aatattggtt tttttttttt tttttttaaat aagtcacagt    1740 cctgttgtca aaactctaat agacagcaaa gagggtctgt accgtagact tcacagtttt    1800 cagttttttaa tgattgccag tggaggggct tcttcagcac agagacccccc cactgtgtcc   1860 agggaccccc tctgccaggt ggaggtgtgt ccaggggctg gggaagccga gacgggcact    1920
ccctctgccg gccggcagcg tggccctgag catggcaagg gggtctgtct ctgccgatgc    1980
tccttccgcg gcactgactc tgcgccgtgt cacatggttt ttgaatcaca ctgcagctgc    2040
tttccatttt tatatatata taaatatata taaatatata cttttttaaaa ataatttata   2100 aatcttacca aaacttatgc taaatatact ttccagtatg aacgcacagg agagtcccat    2160
cagcaggcgg cattggagtc taggagctca gctgtgtgtc catcaacaca caaattcgta    2220
aaaaacacac atggcctcgc catcgtgggt aaaatcggcc ccacagcacg tctgcaccag    2280
cgggccgtta ctcccatgcc gttcttctgt gtaatattaa gaactgaatg tgaagtttat    2340
agctagcctg ggtgtacctt ttaagaattt tgtaaaccgt ttgtctgtct tttgttactg    2400
ttttatggtg ccaagtatcc tacgttacaa caataatatc atgggagaaa tagaaatagc    2460
ctagtttgct tccaatagaa actgcttttta acatgggctg tatataaaaa tattaaagag   2520
aaacaaaact gtacatttcc tcattgctcc gctacagaca acccatgtca taaccttgtt    2580
gcaaatattt ttctcctata gcagtaagta cagcattaga aggtgattag agagtctgtt    2640
gatgaaacac aaatgtatgt tttattgatt ttactttaga acactacaga gttcctggac    2700
cgggtgaagg cattagctgg gtgtttgtgt gggataaata ctaccactgc aagtgactgc    2760
tgtccgctgc ggaatctgtt cttggtggaa gcacaggtcc gtgtcgctgc tgtggttgcc    2820
gctgtccgcg gttcaacacg gagtccgccc cgcgggtttc agctgttggt cgttctgagg    2880
ggcctttgga agtgaccggt ctggttccta agcaataaaa ttgaccgtgg tgaaaata     2938
```

<210> SEQ ID NO 2
<211> LENGTH: 412
<212> TYPE: PRT
<213> ORGANISM: Homo sapiens
<220> FEATURE:
<221> NAME/KEY: MISC_FEATURE
<223> OTHER INFORMATION: INPP5A Protein GenBank CAI40942.1

<400> SEQUENCE: 2

```
Met Ala Gly Lys Ala Ala Pro Gly Thr Ala Val Leu Leu Val Thr
1               5                   10                  15

Ala Asn Val Gly Ser Leu Phe Asp Asp Pro Glu Asn Leu Gln Lys Asn
            20                  25                  30

Trp Leu Arg Glu Phe Tyr Gln Val Val His Thr His Lys Pro His Phe
        35                  40                  45

Met Ala Leu His Cys Gln Glu Phe Gly Gly Lys Asn Tyr Glu Ala Ser
    50                  55                  60

Met Ser His Val Asp Lys Phe Val Lys Glu Leu Leu Ser Ser Asp Ala
65                  70                  75                  80

Met Lys Glu Tyr Asn Arg Ala Arg Val Tyr Leu Asp Glu Asn Tyr Lys
                85                  90                  95
```

```
Ser Gln Glu His Phe Thr Ala Leu Gly Ser Phe Tyr Phe Leu His Glu
                100                 105                 110

Ser Leu Lys Asn Ile Tyr Gln Phe Asp Phe Lys Ala Lys Lys Tyr Arg
            115                 120                 125

Lys Val Ala Gly Lys Glu Ile Tyr Ser Asp Thr Leu Glu Ser Thr Pro
        130                 135                 140

Met Leu Glu Lys Glu Lys Phe Pro Gln Asp Tyr Phe Pro Glu Cys Lys
145                 150                 155                 160

Trp Ser Arg Lys Gly Phe Ile Arg Thr Arg Trp Cys Ile Ala Asp Cys
                165                 170                 175

Ala Phe Asp Leu Val Asn Ile His Leu Phe His Asp Ala Ser Asn Leu
            180                 185                 190

Val Ala Trp Glu Thr Ser Pro Ser Val Tyr Ser Gly Ile Arg His Lys
        195                 200                 205

Ala Leu Gly Tyr Val Leu Asp Arg Ile Ile Asp Gln Arg Phe Glu Lys
    210                 215                 220

Val Ser Tyr Phe Val Phe Gly Asp Phe Asn Phe Arg Leu Asp Ser Lys
225                 230                 235                 240

Ser Val Val Glu Thr Leu Cys Thr Lys Ala Thr Met Gln Thr Val Arg
                245                 250                 255

Ala Ala Asp Thr Asn Glu Val Val Lys Leu Ile Phe Arg Glu Ser Asp
            260                 265                 270

Asn Asp Arg Lys Val Met Leu Gln Leu Glu Lys Lys Leu Phe Asp Tyr
        275                 280                 285

Phe Asn Gln Glu Val Phe Arg Asp Asn Asn Gly Thr Ala Leu Leu Glu
290                 295                 300

Phe Asp Lys Glu Leu Ser Val Phe Lys Asp Arg Leu Tyr Glu Leu Asp
305                 310                 315                 320

Ile Ser Phe Pro Pro Ser Tyr Pro Tyr Ser Glu Asp Ala Arg Gln Gly
                325                 330                 335

Glu Gln Tyr Met Asn Thr Arg Cys Pro Ala Trp Cys Asp Arg Ile Leu
            340                 345                 350

Met Ser Pro Ser Ala Lys Glu Leu Val Leu Arg Ser Glu Ser Glu Glu
        355                 360                 365

Lys Val Val Thr Tyr Asp His Ile Gly Pro Asn Val Cys Met Gly Asp
    370                 375                 380

His Lys Pro Val Phe Leu Ala Phe Arg Ile Met Pro Gly Ala Gly Lys
385                 390                 395                 400

Pro His Ala His Val His Lys Cys Cys Val Val Gln
                405                 410

<210> SEQ ID NO 3
<211> LENGTH: 20
<212> TYPE: DNA
<213> ORGANISM: Artificial Sequence
<220> FEATURE:
<223> OTHER INFORMATION: The primer used for INPP5A q-Real-Time PCR

<400> SEQUENCE: 3
ttgcagactg tgcctttgac                                           20

<210> SEQ ID NO 4
<211> LENGTH: 20
<212> TYPE: DNA
<213> ORGANISM: Artificial Sequence
<220> FEATURE:
```

-continued

```
<223> OTHER INFORMATION: The primer used for INPP5A q-Real-Time PCR

<400> SEQUENCE: 4
aaaccttctc gaatcgctga                                              20

<210> SEQ ID NO 5
<211> LENGTH: 23
<212> TYPE: DNA
<213> ORGANISM: Artificial Sequence
<220> FEATURE:
<223> OTHER INFORMATION: The primers used for ACTB q-Real-Time PCR

<400> SEQUENCE: 5
tcatgaagtg tgacgtggac atc                                          23

<210> SEQ ID NO 6
<211> LENGTH: 24
<212> TYPE: DNA
<213> ORGANISM: Artificial Sequence
<220> FEATURE:
<223> OTHER INFORMATION: The primers used for ACTB q-Real-Time PCR

<400> SEQUENCE: 6
caggaggagc aatgatcttg atct                                         24
```

IDENTIFICATION AND TREATMENT OF CANCER SUBSETS

CROSS REFERENCE TO RELATED APPLICATIONS

This application claims the priority of U.S. provisional applications entitled IDENTIFICATION AND TREATMENT OF CANCER SUBSETS, with application No. 61/393,065, filed on 14 Oct. 2010, which is hereby incorporated by reference in its entirety.

STATEMENT REGARDING FEDERALLY SPONSORED RESEARCH

This invention was made with government support under CA27502 awarded by the National Institutes of Health. The government has certain rights in this invention.

FIELD OF THE INVENTION

The present invention is related to skin cancer, and more specifically, methods and kits for skin squamous cell carcinoma prognosis, diagnosis, theranosis and treatment using INPP5A expression as an indication.

BACKGROUND OF THE INVENTION

Over 1,000,000 non-melanoma skin cancers are diagnosed annually in the US, making these the most common type of cancer and the fifth most costly cancer type in the Medicare population. Approximately eighty percent of nonmelanoma skin cancers are basal-cell carcinomas, and twenty percent are squamous-cell carcinomas (SCC). Unlike almost all basal-cell carcinomas, cutaneous squamous-cell carcinomas are associated with a substantial risk of metastasis. The principal precursor of cutaneous squamous-cell carcinoma is actinic keratosis (AK). AK has been described as a type of carcinoma in situ or SCCIS, in which carcinoma involves only the epidermis. Some of AK may evolve into invasive squamous-cell carcinoma. Options for treating AK include cryosurgery, electrodesiccation and curettage, topical fluorouracil, dermabrasion, and laser resurfacing.

On histological examination actinic keratoses and invasive squamous-cell carcinomas exhibit a spectrum of neoplastic changes. From a therapeutic standpoint, it is impractical and unnecessary to treat each individual keratotic lesion. Only patients with many lesions are followed closely, and thus, many events or tumor progression are undetected until at an advanced stage. Therefore, accurate prognostic markers and targeted therapies as well as more effective early chemopreventive strategies are necessary so that evolving squamous-cell carcinomas can be detected and treated expeditiously.

BRIEF SUMMARY OF THE INVENTION

Provided herein is a method of identifying a tumor responding to INPP5A metabolites. The method generally comprises obtaining a sample of the tumor; adding a first reagent to a mixture comprising the sample, wherein the first reagent is capable of detecting a marker comprising sequence selected from the group consisting of SEQ ID NO. 1 and SEQ ID NO. 2; subjecting the mixture to conditions that allow the detection of marker expression; and classifying the tumor into a INPP5A metabolites-sensitive group based on reduced expression of INPP5A in comparison to a control. In the general method, when the marker comprises SEQ ID NO. 1, the first reagent comprises a first and a second oligonucleotide capable of binding SEQ ID NO:1; and the method for detection of the marker is selected from the group consisting of PCR- and hybridization-based methods. In one example, at least one of the first and the second oligonucleotides comprises a label comprising a fluorescent label selected from the group consisting of FAM, dR110, 5-FAM, 6FAM, dR6G, JOE, HEX, VIC, TET, dTAMRA, TAMRA, NED, dROX, PET, BHQ+, Gold540, and LIZ. In this example, the general method may further comprise isolating total RNA from the sample; performing reverse transcription of total RNA isolated to obtain cDNA; and subjecting cDNA to conditions that allow nucleic acid amplification by the first and second oligonucleotides.

In another example, the first nucleic acid of the general method is affixed to a substrate; and the method may comprise performing array-based analysis of SEQ ID NO. 1 to the sample.

In the general method, when the marker comprises SEQ ID NO. 2, the first reagent comprises a first antibody capable of binding a region of SEQ ID NO. 2. Further, the first antibody comprises a first label selected from the group consisting of a fluorescent compound, an enzyme, a radioisotope, and a ligand. In some examples, the general method may further comprise adding a second antibody to the mixture, wherein the second antibody is capable of binding to the first antibody. Optionally, the second antibody may comprise a second label selected from the group consisting of a fluorescent compound, an enzyme, a radioisotope, and a ligand. The general method of detecting the marker may also include determining the deletion of INPP5A at chromosome 10q26.3.

The samples in the general method may be in a form selected from the group consisting of an FFPE sample, a frozen sample, and a fresh tumor biopsy. The control in the general method may be selected from the group consisting of normal tissue, normal tissue adjacent to the tumor, tissue from a less progressed tumor from the same subject. The method may further comprise collecting a sample from a subject selected from a group consisting of a human, a companion animal, and a livestock animal. The tumor of the sample in the general method may be squamous cell carcinoma (SCC), squamous-cell carcinoma in situ (SCCIS) or actinic keratosis (AK). Alternatively, the sample in the general method may be suspected to be a skin squamous cell carcinoma (SCC), squamous-cell carcinoma in situ (SCCIS) or actinic keratosis (AK).

Also provided herein is a method of assessing a risk of progression of skin carcinoma in a subject, the method comprising: obtaining a skin sample from the patient; adding a reagent capable of binding a marker selected from the group consisting of SEQ ID NO. 1 and SEQ ID NO. 2 to a mixture comprising the sample; subjecting the mixture to conditions that allow detection of the marker expression; and labeling the subject as having risk of skin carcinoma progression based on the reduced expression of INPP5A in comparison to a control. Since loss of INPP5A was shown to be present in a significant percentage of all stages of SCC, from precursor to metastatic disease, observing loss at AK, SCCIS, or local SCC indicates a risk that the lesion where the loss is observed in may continue to evolve through the stages to eventually become metastatic SCC. In this method, if the sample comprises an actinic keratosis, then the progression of the skin carcinoma may comprise progression to squamous cell carcinoma or metastatic squamous cell carcinoma. If the sample in the method comprises a squamous cell carcinoma in situ, then the progression of the skin carcinoma may comprise progression to squamous cell carcinoma or metastatic squamous cell carcinoma. Alternatively, if the sample comprises a squamous cell carcinoma, then the progression of the disease comprises progression to metastatic squamous cell carcinoma. The detection of the marker expression in the general method may be selected from the group consisting of PCR-based, hybridization-based, array-based methods and any combinations thereof.

Further provided herein is a method of treating a subject having skin squamous cell carcinoma at various stages, and the method comprises: obtaining a sample from a subject; determining tumor cell responsiveness to INPP5A metabolites of the sample; administering a pharmaceutical composition comprising one or more INPP5A metabolites or a pharmaceutically acceptable salt thereof to the subject; wherein the subject has tumor cell determined to be responsive to INPP5A metabolites. In one example, said method may further comprise: adding to a mixture comprising the sample, a reagent capable of binding a marker selected from the group consisting of SEQ ID NO. 1 and SEQ ID NO. 2; subjecting the mixture to conditions that allow detection of the marker expression; wherein reduced expression of the marker in comparison to a control indicates the cell responsiveness to INPP5A metabolites. The control of the method is selected from, depending on the stage of the sample tissue, the group consisting of normal skin tissue, normal skin tissue adjacent to the tumor of the same subject, skin tissue from a less progressed tumor including actinic keratosis and squamous cell carcinoma in situ of the same subject. In one example, the pharmaceutical composition of the method comprises IP6 or a pharmaceutically acceptable salt thereof, wherein, the pharmaceutical composition of the method causes cessation or reduction of cell proliferation in actinic keratosis, squamous cell carcinoma in situ, squamous cell carcinoma or metastasized squamous cell carcinoma, and restores cell differentiation resulting in cell death.

In said method, determining the tumor cell responsiveness to INPP5A metabolites of the sample is a step of detecting the deletion of INPP5A at chromosome 10q26.3. In some examples, the sample subjected to the method comprises a skin sample. Further, the sample may comprise a cell selected from the group consisting of actinic keratosis cell; squamous cell carcinoma in situ cell, squamous cell carcinoma cell, and metastatic squamous cell carcinoma cell.

Further provided herein is a kit for assessing skin tumor responsiveness to INPP5A metabolites. The kit generally comprises: a first reagent capable of specific detection of a marker selected from the group consisting of SEQ ID NO. 1 and SEQ ID NO. 2; and an indication signifying a result associated with INPP5A metabolite-sensitivity of the tumor. In one example, the first reagent comprising a first and a second oligonucleotide capable of binding SEQ ID NO. 1, and at least one of the first and the second oligonucleotides comprises a label comprising a fluorescence moiety or compound selected from the group consisting of FAM, dR110, 5-FAM, 6FAM, dR6G, JOE, HEX, VIC, TET, dTAMRA, TAMRA, NED, dROX, PET, BHQ+, Gold540, and LIZ 31. In another example, the first reagent of the kit comprises a first antibody capable of binding a region in SEQ ID NO. 2, and the first antibody comprises a first label selected from the group consisting of a fluorescent compound, an enzyme, a radioisotope, and a ligand. The kit may further comprise a second antibody capable of binding to the first antibody comprising a second label selected from the group consisting of a fluorescent compound, an enzyme, a radioisotope, and a ligand. The result contained in the kit is based on the expression level of INPP5A in comparison to a control selected from the group consisting of normal skin tissue, normal skin tissue adjacent to the tumor of the same subject, skin tissue from a less progressed tumor including actinic keratosis and squamous cell carcinoma in situ of the same subject. In other examples, the kit may further comprise a pharmaceutical composition comprising one or more INPP5A metabolites or a pharmaceutically acceptable salt thereof. In one example, the pharmaceutical composition comprises IP6 or a pharmaceutically acceptable salt thereof.

REFERENCE TO COLOR FIGURES

The application file contains at least one figure executed in color. Copies of this patent application publication with color figures will be provided by the Office upon request and payment of the necessary fee.

DETAILED DESCRIPTION OF THE INVENTION

Figure 1:
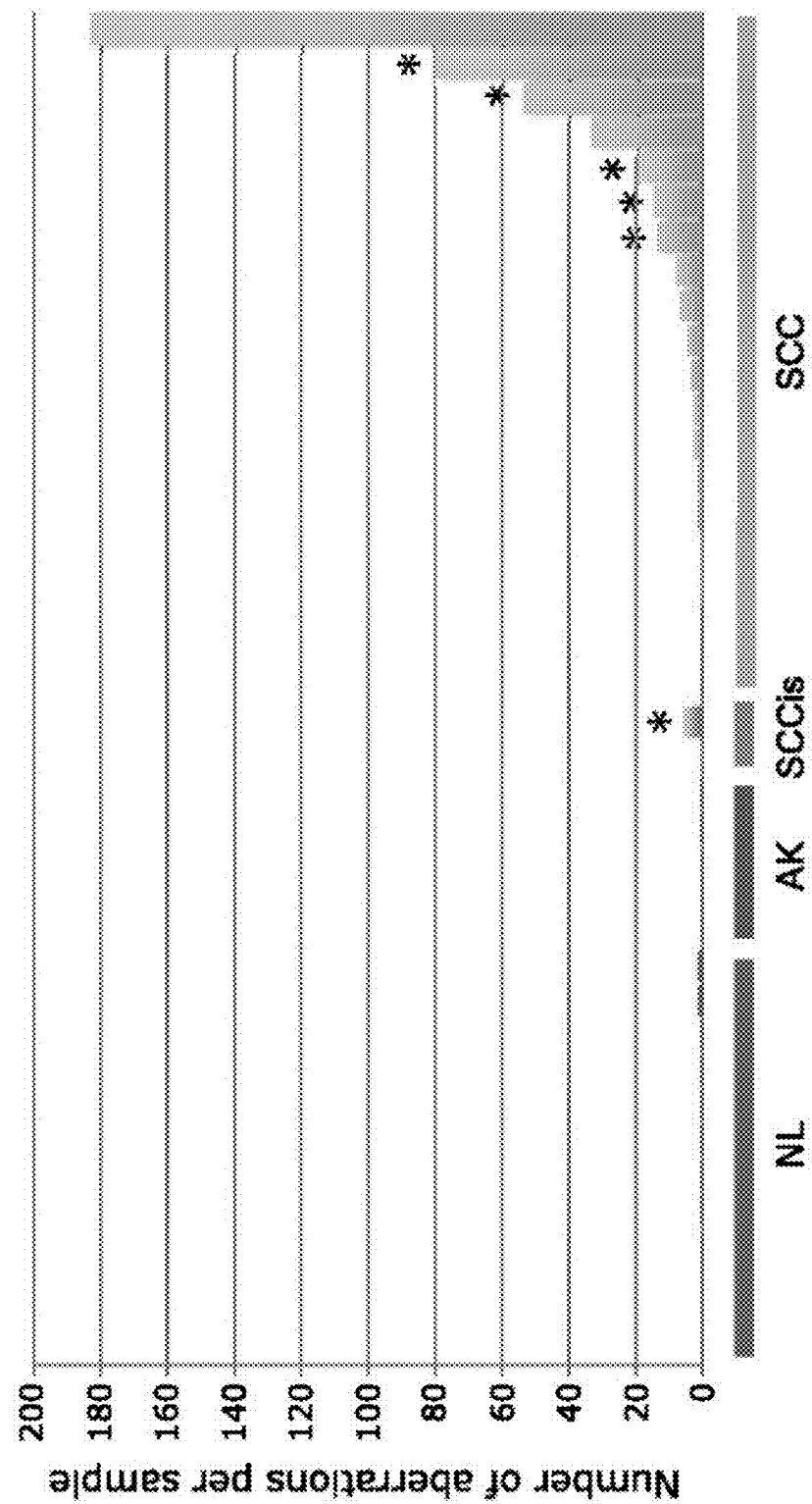
FIG. 1 depicts the distribution of gene and copy number aberrations in 40 tissues examined in this study.

Cutaneous squamous cell carcinoma (SCC) occurs commonly and can metastasize. Identification of specific molecular aberrations and mechanisms underlying the development and progression of cutaneous SCC can lead to better prognostic and therapeutic approaches and more effective chemoprevention strategies.

A genome-wide survey of gene copy number changes in skin tissues identified frequent deletions of INPP5A gene in human SCC tumors. As provided herein, a decrease in INPP5A protein levels is observed in most cutaneous SCCs. This event occurs early in the development of SCC as it can be detected even at the stage of actinic keratosis, a common precursor to SCC. Progressive reduction of INPP5A levels is seen in a subset of SCC patients as the tumor progresses from primary to metastatic stage. Since loss of INPP5A was shown to be present in a significant percentage of all stages of SCC, from precursor to metastatic disease, observing loss at AK, SCCIS, or local SCC indicates a risk that the lesion where the loss is observed in may continue to evolve through the stages to eventually become metastatic SCC.

(I) INPP5A as a Gene Marker

Provided herein is a novel gene, INPP5A, the reduced level of which is associated with development and progression of cutaneous SCC. INPP5A (Type I inositol-1,4,5-trisphosphate 5-phosphatase, UniProtKB/Swiss-Prot Accession Number: Q14642) belongs to a large family of inositol polyphosphate 5-phosphatases. This 40 kDa membrane-associated type I inositol phosphatase has preferential substrate affinity for inositol 1,4,5-trisphosphate (Ins(1,4,5)P3) and inositol 1,3, 4,5 tetrakisphosphate (Ins(1,3,4,5)P4), working mostly as a modulator or the metabolism of inositol phosphates, which are widely used by cells to modulate and regulate a variety of processes. As used in various contexts herein, INPP5A may refer to the nucleic acid form of the gene, or INPP5A may refer to the protein form of the gene.

Further provided herein is the discovery of supplementing inositol phosphate metabolites downstream of the enzyme INPP5A, for example, IP6, for reversal of cancerous cell proliferation to cancer cell death in skin SCC. Therefore, one aspect of the invention provides a method of identifying a tumor responsive to INPP5A metabolites. In particular, based on the finding that reduced INPP5A expression, including the mRNA and the protein level, in a subset of skin SCC is associated with the disease progression as early as AK stage, it has been found that by supplying at least one of the downstream metabolites of INPP5A to this subset of cancerous cells, these cells are responsive to the administration of the metabolite, cancer cell proliferation can be ceased, and cell differentiation can be restored, leading to cancer cell death. In one embodiment, the identified subset of tumor cells with INPP5A deletion is given a supplement of at least one metabolite selected from the group including $Ins(1,3,4)P_3$, $Ins(1,3,4,6)P_4$, $Ins(1,3,4,5,6)P_5$, and $Ins(1,2,3,4,5,6)P_6$ (IP6), such that the supplement of INPP5A metabolite leads to cancer cell death. In one preferred embodiment, the identified subset of tumor cell with INPP5A deletion is given a supplement of IP6.

Generally, the present invention provides a marker associated with tumor cell's responsiveness to INPP5A metabolites. A marker may be any molecular structure produced by a cell, expressed inside the cell, accessible on the cell surface, or secreted by the cell. A marker may be any protein, carbohydrate, fatty acid, nucleic acid, catalytic site, or any combination of these such as an enzyme, glycoprotein, cell membrane, virus, a particular cell, or other uni- or multimolecular structure. A marker may be represented by a sequence of a nucleic acid or any other molecules derived from the nucleic acid. Examples of such nucleic acids include miRNA, tRNA, siRNA, mRNA, cDNA, genomic DNA sequences, or complementary sequences thereof. Alternatively, a marker may be represented by a protein sequence. The concept of a marker is not limited to the exact nucleic acid sequence or protein sequence or products thereof, rather it encompasses all molecules that may be detected by a method of assessing the expression of the marker. Without being limited by the theory, the reduced INPP5A expression, including the mRNA and the protein level, in a subset of skin SCC may be caused by deletion of INPP5A gene, different alleles of INPP5A gene, a mutation in the INPP5A gene, gene expression regulation abnormally, increased INPP5A mRNA or protein degradation, all of which may result in lower expression of INPP5A individually or in any combination.

Therefore, examples of molecules encompassed by a marker represented by a particular sequence further include alleles of the gene used as a marker. An allele includes any form of a particular nucleic acid that may be recognized as a form of the particular nucleic acid on account of its location, sequence, or any other characteristic that may identify it as being a form of the particular gene. Alleles include but need not be limited to forms of a gene that include point mutations, silent mutations, deletions, frameshift mutations, single nucleotide polymorphisms (SNPs), inversions, translocations, heterochromatic insertions, and differentially methylated sequences relative to a reference gene, whether alone or in combination. An allele of a gene may or may not produce a functional protein; may produce a protein with altered function, localization, stability, dimerization, or protein-protein interaction; may have overexpression, underexpression or no expression; may have altered temporal or spatial expression specificity. An allele may also be called a mutation or a mutant. An allele may be compared to another allele that may be termed a wild type form of an allele. In some cases, the wild type allele is more common than the mutant.

A mutation in INPP5A gene that causes decreased activity of INPP5A in a test subject or a biological sample may also be called a loss-of-function mutation. A mutation may be any detectable change in genetic material such as DNA, or a corresponding change in the RNA or protein product of that genetic material. A mutant may be any biological material in which one or more mutations are detected when compared to a control material. Examples of mutations include gene mutations, in which the DNA sequence of a gene or any controlling elements surrounding the gene is altered. Controlling elements include promoter, enhancer, suppressor or silencing elements capable of controlling a given gene. Other examples of mutations include alterations in the products of DNA expression such as RNA or protein that result from corresponding mutations in the DNA. Mutants may also be interchangeably called variants. The concept of a mutant includes any change in DNA sequence specific to the tumor cell (not present in DNA prepared from normal, non-neoplastic tissues).

Loss-of-function mutations display decreased total INPP5A activity in the test subject or biological sample in comparison with a control, e.g., a healthy subject or a sample without SCC or SCC precursors (standard sample). Therefore, the activity of INPP5A in a subject or a sample carrying loss-of-function mutation in INPP5A is 5%, 10%, 20%, 30%, 40%, 50%, 60%, 70%, 80%, 90%, 95%, 99% relative to that activity in a healthy subject or a standard sample. The decreased activity of INPP5A in a subject or a sample carrying loss-of-function mutation may result from, for example, decreased basal INPP5A activity, lessened activation, faster degradation, or under-expression, e.g., due to decreased mRNA expression level, reduced substrate binding, promiscuous or inappropriate substrate binding, impaired recycling resulting in abnormal signaling, increased degradation, or enzyme activation.

A reduced expression level of INPP5A mRNA may result from, for example, a mutation in a non-coding region of a INPP5A gene or a mutation in a coding or non-coding gene involved in INPP5A transcription or translation. The expression level of INPP5A can be determined, for example, by comparing INPP5A mRNA or the level of INPP5A protein in a test subject as compared to a control, for example, by comparing the SCC tumor to normal skin tissue (e.g., a normal adjacent skin tissue sample).

The INPP5A marker provided herein also included conserved variants encompassing any mutation or other variant in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Depending on the location of the mutation in the overall context of the protein, some substitutions may have little or no effect on the apparent molecular weight or isoelectric point of the protein or polypeptide. However some conserved variants have been found to alter protein conformation and function, including several variants discovered and disclosed herein.

Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. The concept of a variant further encompasses a polypeptide or enzyme which has at least 60%, 75%, 85%, 90%, or 95%, amino acid identity as determined by algorithms, such as, BLAST or FASTA, and which has the same or substantially similar properties and/or activities as the native or parent protein or enzyme to which it is compared.

One example of such a variant is a loss-of-function variant. Loss-of-function variants of polypeptides encompass any variant in which a change in one or more amino acid residues in a protein or enzyme improves the activity of the polypeptide. Examples of activities of a polypeptide that may be impaired by a change resulting in a gain of function variant include but are not limited to enzymatic activity, binding affinity, phosphorylation or dephosphorylation efficiency, activation or deactivation by a regulatory protein, or any other activity or property of a protein that may be quantitatively measured by some method now known or yet to be disclosed.

Proteins that possess a common evolutionary origin may be homologous or similar to one another. Examples of homologous or similar proteins include proteins from superfamilies (e.g., the immunoglobulin superfamily) and homologous proteins from different species. Such proteins and their encoding genes have sequence homology with one another. The homology may be expressed in terms of percent similarity or the presence of specific residues or motifs at conserved positions.

The presence or absence of an allele of the gene marker may be detected through the use of any process known in the (II) Methods of Detecting Differential Expression of INPP5A in a Sample A. Method for Identifying Tumor Cells Responsive to INPP5A Metabolites In one embodiment of the invention, the identification of the INPP5A metabolite responsive tumor cells generally includes detecting tumor cells with reduced INPP5A mRNA level. In another embodiment of the present invention, the identification of the INPP5A metabolite responsive tumor cells generally includes detecting tumor cells with reduced INPP5A protein level. In one preferred embodiment, the INPP5A metabolite is IP6.

Expression of a marker may be assessed by any number of methods used to detect material derived from a nucleic acid template. Differential expression of a marker may be assessed or quantified by a detector, an instrument containing a detector, or by an aided or unaided human eye. Exemplary methods for nucleic acid detection and/or quantification include, but are not limited to, microarray analysis, RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing, or any other method of detecting a specific nucleic acid now known or yet to be disclosed. Exemplary methods for assessing protein expression include, for example, flow cytometry, immunohistochemistry, ELISA, Western blot, and immunoaffinity chromatography, HPLC, mass spectrometry, protein microarray analysis, PAGE analysis, isoelectric focusing, 2-D gel electrophoresis, or any enzymatic assay. Methods of detecting expression may include, for example, methods of purifying nucleic acid, protein, or some other material depending on a nucleic acid-based or protein-based approach. Any method of nucleic acid purification may be used, depending on the type of marker (i.e., nucleic acid or protein), examples include phenol alcohol extraction, ethanol extraction, guanidium isothionate extraction, gel purification, size exclusion chromatography, cesium chloride preparations, and silica resin preparation. Any method of protein purification may be used, non-limiting examples of which include size exclusion chromatography, hydrophobic interaction chromatography, ion exchange chromatography, affinity chromatography (including affinity chromatography of tagged proteins), metal binding, immunoaffinity chromatography, and HPLC.

(a) PCR Based Methods

Nucleic acids may be selectively and specifically amplified from a template nucleic acid contained in a sample. In some nucleic acid amplification methods, the copies are generated exponentially. Examples of nucleic acid amplification methods known in the art include: polymerase chain reaction (PCR), ligase chain reaction (LCR), self-sustained sequence replication (3SR), nucleic acid sequence based amplification (NASBA), strand displacement amplification (SDA), amplification with Qβ replicase, whole genome amplification with enzymes such as φ29, whole genome PCR, in vitro transcription with T7 RNA polymerase or any other RNA polymerase, or any other method by which copies of a desired sequence are generated.

With PCR, it is possible to amplify a single copy of a specific target sequence in genomic DNA or total RNA to a level detectable by several different methodologies, for example, hybridization with a labeled probe, incorporation of biotinylated primers followed by avidin-enzyme conjugate detection, and, incorporation of $^{32}$P-labeled deoxynucleotide triphosphates, such as dCTP or dATP, into the amplified segment. Generally, nucleic acid based probes and primers are complementary to a sequence within the target DNA sequence region. In addition to genomic DNA, any oligonucleotide or polynucleotide sequence can be amplified with an appropriate set of primer molecules. In particular, the amplified segments created by the PCR process itself are, themselves, efficient templates for subsequent PCR amplifications.

PCR generally involves the mixing of a nucleic acid sample, two or more primers that are designed to recognize the template DNA, a DNA polymerase, which may be a thermostable DNA polymerase such as Taq or Pfu, and deoxyribose nucleoside triphosphates (dNTP's). Reverse transcription PCR, quantitative reverse transcription PCR, and quantitative real time reverse transcription PCR are other specific examples of PCR. In general, the reaction mixture is subjected to temperature cycles comprising a denaturation stage (typically 80-100° C.), an annealing stage with a temperature that is selected based on the melting temperature (Tm) of the primers and the degeneracy of the primers, and an extension stage (for example 40-75° C.). In real-time PCR analysis, additional reagents, methods, optical detection systems, and devices known in the art are used that allow a measurement of the magnitude of fluorescence in proportion to concentration of amplified DNA. In such analyses, incorporation of fluorescent dye into the amplified strands may be detected or measured.

Alternatively, labeled probes that bind to a specific sequence during the annealing phase of the PCR may be used with primers. Labeled probes release their fluorescent tags during the extension phase so that the fluorescence level may be detected or measured. Generally, probes are complementary to a sequence within the target sequence downstream from either the upstream or downstream primer. Probes may include one or more label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent), stain, enzyme, or nonradioactive metal. Specific examples include, but are not limited to: fluorescein, biotin, digoxigenin, alkaline phosphatese, biotin, streptavidin, $^{3}$H, $^{14}$C, $^{32}$P, $^{35}$S, or any other compound capable of emitting radiation, rhodamine, 4-(4'-dimethylamino-phenylazo) benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected. The label may also include one or more fluorescent dyes optimized for use in genotyping. Examples of dyes facilitating the reading of the target amplification include, but are not limited to: CAL-Fluor Red 610, CAL-Fluor Orange 560, dR110, 5-FAM, 6FAM, dR6G, JOE, HEX, VIC, TET, dTAMRA, TAMRA, NED, dROX, PET, BHQ+, Gold540, and LIZ.PCR facilitating the reading of the target amplification.

Either primers or primers along with probes allow a quantification of the amount of specific template DNA present in the initial sample. In addition, RNA may be detected by PCR analysis by first creating a DNA template from RNA through a reverse transcriptase enzyme. The marker expression may be detected by quantitative PCR analysis facilitating genotyping analysis of the samples.

An illustrative example, using dual-labeled oligonucleotide probes in PCR reactions is disclosed in U.S. Pat. No. 5,716,784 to DiCesare. In one example of the PCR step of the multiplex Real Time-PCR/PCR reaction of the present invention, the dual-labeled fluorescent oligonucleotide probe binds to the target nucleic acid between the flanking oligonucleotide primers during the annealing step of the PCR reaction. The 5' end of the oligonucleotide probe contains the energy transfer donor fluorophore (reporter fluor) and the 3' end contains the energy transfer acceptor fluorophore (quenching fluor). In the intact oligonucleotide probe, the 3' quenching fluor quenches the fluorescence of the 5' reporter fluor. However, when the oligonucleotide probe is bound to the target nucleic acid, the 5' to 3' exonuclease activity of the DNA polymerase, e.g., Taq DNA polymerase, will effectively digest the bound labeled oligonucleotide probe during the amplification step. Digestion of the oligonucleotide probe separates the 5' reporter fluor from the blocking effect of the 3' quenching fluor. The appearance of fluorescence by the reporter fluor is detected and monitored during the reaction, and the amount of detected fluorescence is proportional to the amount of fluorescent product released. Examples of apparatus suitable for detection include, e.g. Applied Biosystems™ 7900HT real-time PCR platform and Roche's 480 LightCycler, the ABI Prism 7700 sequence detector using 96-well reaction plates or GENEAMP PC System 9600 or 9700 in 9600 emulation mode followed by analysis in the ABA Prism Sequence Detector or TAQMAN LS-50B PCR Detection System. The labeled probe facilitated multiplex Real Time-PCR/PCR can also be performed in other real-time PCR systems with multiplexing capabilities.

"Amplification" is a special case of nucleic acid replication involving template specificity. Amplification may be a template-specific replication or a non-template-specific replication (in other words, replication may be specific template-dependent or not). Template specificity is here distinguished from fidelity of replication (synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

The term "template" refers to nucleic acid originating from a sample that is analyzed for the presence of a molecule of interest. In contrast, "background template" or "control" is used in reference to nucleic acid other than sample template that may or may not be present in a sample. Background template is most often inadvertent. It may be the result of carryover, or it may be due to the presence of nucleic acid contaminants sought to be purified out of the sample. For example, nucleic acids from organisms other than those to be detected may be present as background in a test sample.

In addition to primers and probes, template specificity is also achieved in some amplification techniques by the choice of enzyme. Amplification enzymes are enzymes that, under the conditions in which they are used, will process only specific sequences of nucleic acid in a heterogeneous mixture of nucleic acid. Other nucleic acid sequences will not be replicated by this amplification enzyme. Similarly, in the case of T7 RNA polymerase, this amplification enzyme has a stringent specificity for its own promoters (Chamberlin et al. (1970) Nature (228):227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics (4):560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) PCR Technology, Stockton Press).

The term "amplifiable nucleic acid" refers to nucleic acids that may be amplified by any amplification method. It is contemplated that "amplifiable nucleic acid" will usually comprise "sample template." The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

In some forms of PCR assays, quantification of a target in an unknown sample is often required. Such quantification is often in reference to the quantity of a control sample. The control sample DNA may be co-amplified in the same tube in a multiplex assay or may be amplified in a separate tube. Generally, the control sample contains DNA at a known concentration. The control sample DNA may be a plasmid construct comprising only one copy of the amplification region to be used as quantification reference. To calculate the quantity of a target in an unknown sample, various mathematical models are established. Calculations are based on the comparison of the distinct cycle determined by various methods, e.g., crossing points (CP) and cycle threshold values (Ct) at a constant level of fluorescence; or CP acquisition according to established mathematic algorithm.

The algorithm for Ct values in Real Time-PCR calculates the cycle at which each PCR amplification reaches a significant threshold. The calculated Ct value is proportional to the number of target copies present in the sample, and the Ct value is a precise quantitative measurement of the copies of the target found in any sample. In other words, Ct values represent the presence of respective target that the primer sets are designed to recognize. If the target is missing in a sample, there should be no amplification in the Real Time-PCR reaction.

Alternatively, the Cp value may be utilized. A Cp value represents the cycle at which the increase of fluorescence is highest and where the logarithmic phase of a PCR begins. The LightCycler® 480 Software calculates the second derivatives of entire amplification curves and determines where this value is at its maximum. By using the second-derivative algorithm, data obtained are more reliable and reproducible, even if fluorescence is relatively low.

The various and non-limiting embodiments of the PCR-based method detecting marker expression level as described herein may comprise one or more probes and/or primers. Generally, the probe or primer contains a sequence complementary to a sequence specific to a region of the nucleic acid of the marker gene. A sequence having less than 60% 70%, 80%, 90%, 95%, 99% or 100% identity to the identified gene sequence may also be used for probe or primer design if it is capable of binding to its complementary sequence of the desired target sequence in marker nucleic acid.

(b) Hybridization Based Methods

In addition to PCR, gene expression analysis may also be performed using a probe that is capable of hybridizing to a nucleic acid sequence of interest. The term "hybridization" refers to the pairing of complementary nucleic acids. Hybridization and the strength of hybridization (i.e. the strength of the association between the nucleic acids) is impacted by such factors as the degree of complementary between the nucleic acids, stringency of the conditions involved, the Tm of the formed hybrid, and the G:C ratio within the nucleic acids. A single molecule that contains pairing of complementary nucleic acids within its structure is said to be "self-hybridized."

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" when used in relation to nucleic acids refers to a degree of complementarity. There may be partial homology, wherein some of the nucleic acids of a first sequence are identical to the corresponding nucleic acids in a second sequence, or complete homology, wherein the sequences are identical. "Sequence identity" refers to a measure of relatedness between two or more nucleic acids, and is given as a percentage with reference to the total comparison length. The identity calculation takes into account those nucleotide residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence, one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding, or hybridization, of a sequence that is completely homologous to a target under conditions of low stringency. This is not to say that conditions of low stringency are such that non-specific binding is permitted; low stringency conditions require that the binding of two sequences to one another be a specific and selective interaction. The absence of non-specific binding may be tested by the use of a second target which lacks even a partial degree of complementarity, for example, less than about 30% identity. In the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

Low stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components, for example, the presence or absence of formamide, dextran sulfate, polyethylene glycol, are considered and the hybridization solution may be varied to generate conditions of low stringency hybridization different from, but equivalent to, the above listed conditions. In addition, conditions are known in the art that promote hybridization under conditions of high stringency, for example, increasing the temperature of the hybridization and/or wash steps, the use of formamide in the hybridization solution, etc.

When used in reference to a double-stranded nucleic acid sequence such as a cDNA or genomic clone, the term "substantially homologous" refers to any probe that can hybridize to either or both strands of the double-stranded nucleic acid sequence under conditions of low to high stringency as described above.

When used in reference to a single-stranded nucleic acid sequence, the term "substantially homologous" refers to any probe that can hybridize, or is the complement of, the single-stranded nucleic acid sequence under conditions of low to high stringency as described above.

The term "Tm" refers to the "melting temperature" of a nucleic acid. The melting temperature is the temperature at which a population of double-stranded nucleic acid molecules becomes half dissociated into single strands. The equation for calculating the Tm of nucleic acids is well known in the art. As indicated by standard references, a simple estimate of the Tm value may be calculated by the equation: $Tm=81.5+0.41(\% G+C)$, when a nucleic acid is in aqueous solution at 1 M NaCl (See for example, Anderson and Young, Quantitative Filter Hybridization (1985) in Nucleic Acid Hybridization). Other references include more sophisticated computations that take structural as well as sequence characteristics into account for the calculation of Tm.

As used herein the term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

Probes for hybridization may comprise nucleic acids, oligonucleotides (DNA or RNA), proteins, protein complexes, conjugates, natural ligands, small molecules, nanoparticles, or any combination of molecules that includes one or more of the above, or any other molecular entity capable of specific binding to any allele, whether such molecular entity exists now or is yet to be disclosed. In one aspect of the invention, the probe comprises an oligonucleotide, as described above. Other methods used to assess expression include the use of natural or artificial ligands capable of specifically binding a marker in its protein or peptide form. Such ligands include antibodies, antibody complexes, conjugates, natural ligands, small molecules, nanoparticles, or any other molecular entity capable of specific binding to a marker. The term "antibody" is used herein in the broadest sense and refers generally to a molecule that contains at least one antigen binding site that immunospecifically binds to a particular antigen target of interest. The term antibody thus includes, but is not limited to, native antibodies and variants thereof, fragments of native antibodies and variants thereof, peptibodies and variants thereof, and antibody mimetics that mimic the structure and/or function of an antibody or a specified fragment or portion thereof, including single chain antibodies and fragments thereof. The term thus includes full length antibodies and/or their variants as well as immunologically active fragments thereof, thus encompassing antibody fragments capable of binding to a biological molecule (such as an antigen or receptor) or portions thereof, including but not limited to Fab, Fab_, F(ab_)2, facb, pFc_, Fd, Fv or scFv (See, e.g., CURRENT PROTOCOLS IN IMMUNOLOGY, (Colligan et al., eds., John Wiley & Sons, Inc., NY, 1994-2001)).

Ligands may be associated with a label such as a radioactive isotope or chelate thereof, dye (fluorescent or nonfluorescent), stain, enzyme, metal, or any other substance capable of aiding a machine or a human eye from differentiating a cell expressing a marker from a cell not expressing a marker. Additionally, expression may be assessed by monomeric or multimeric ligands associated with substances capable of killing the cell. Such substances include protein or small molecule toxins, cytokines, pro-apoptotic substances, pore forming substances, radioactive isotopes, or any other substance capable of killing a cell.

In some aspects of the invention, the expression level of a marker gene may be established by binding to probes in a media or on a microarray such as a DNA chip. Examples of DNA chips include chips in which a number of single stranded oligonucleotide probes are affixed to a solid substrate such as silicon glass. Oligonucleotides with a sequence complementary to an allele are capable of specifically binding to that allele to the exclusion of alleles that differ from the specific allele by one or more nucleotides. Labeled sample DNA is hybridized to the oligonucleotides and detection of the label is correlated with binding of the sample, and consequently, the presence of the allele in the sample.

A nucleic acid probe may be affixed to a substrate. Alternatively, a sample may be affixed to the substrate. A probe or sample may be covalently bound to the substrate or it may be bound by some non covalent interaction including electrostatic, hydrophobic, hydrogen bonding, Van Der Waals, magnetic, or any other interaction by which a probe such as an oligonucleotide probe may be attached to a substrate while maintaining its ability to recognize the allele to which it has specificity. A substrate may be any solid or semi-solid material onto which a probe may be affixed, either singly or in the presence of one or more additional probes or samples as is exemplified in a microarray. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array or an in situ PCR reaction, and the nucleic acid probe may include a label as described herein.

(c) Sample and Subject

Differential expression encompasses any detectable difference between the expression of a marker in one sample relative to the expression of the marker in another sample. Examples include but are not limited to differential staining of cells in an IHC assay configured to detect a marker, differential detection of bound RNA on a microarray to which a sequence capable of binding to the marker is bound, differential results in measuring Real Time-PCR measured in the number of PCR cycles necessary to reach a particular optical density at a wavelength at which a double stranded DNA binding dye (e.g., SYBR Green) incorporates, differential results in measuring label from a reporter probe used in a real-time PCR reaction, differential detection of fluorescence on cells using a flow cytometer, differential intensities of bands in a Northern blot, differential intensities of bands in an RNAse protection assay, differential cell death measured by apoptotic markers, differential cell death measured by shrinkage of a tumor, or any method that allows a detection of a difference in signal between one sample or set of samples and another sample or set of samples.

The expression of the marker in a sample may be compared to a level of expression predetermined to predict the presence or absence of a particular physiological characteristic. The level of expression may be derived from a single control or a set of controls. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources. Comparison of the expression of the marker in the sample to a particular level of expression results in a prediction that the sample exhibits or does not exhibit the cellular or physiological characteristic.

The sample in this general tumor identification method is preferably a biological sample from a subject. The term "sample" or "biological sample" is used in its broadest sense. Depending upon the embodiment of the invention, for example, a sample may comprise a bodily fluid including whole blood, serum, plasma, urine, saliva, cerebral spinal fluid, semen, vaginal fluid, pulmonary fluid, tears, perspiration, mucus and the like; an extract from a cell, chromosome, organelle, or membrane isolated from a cell; a cell; genomic DNA, RNA, or cDNA, in solution or bound to a substrate; a tissue; a tissue print, or any other material isolated in whole or in part from a living subject. In one preferred embodiment, the sample is skin tissue. Biological samples may also include sections of tissues such as biopsy and autopsy samples, and frozen sections taken for histologic purposes such as blood, plasma, serum, sputum, stool, tears, mucus, hair, skin, and the like. Biological samples also include explants and primary and/or transformed cell cultures derived from patient tissues.

The term "subject" is used in its broadest sense. In a preferred embodiment, the subject is a mammal. Non-limiting examples of mammals include humans, dogs, cats, horses, cows, sheep, goats, and pigs. Preferably, a subject includes any human or non-human mammal, including for example: a primate, cow, horse, pig, sheep, goat, dog, cat, or rodent, capable of developing cancer including human patients that are suspected of having cancer, that have been diagnosed with cancer, or that have a family history of cancer.

Cancer cells include any cells derived from a tumor, neoplasm, cancer, precancer, cell line, malignancy, or any other source of cells that have the potential to expand and grow to an unlimited degree. Cancer cells may be derived from naturally occurring sources or may be artificially created. Cancer cells may also be capable of invasion into other tissues and metastasis. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state. In one preferred embodiment, the cancer cell is SCC cell or its precursor Actinic Keratosis cells.

Examples of cancers that could serve as sources of cancer cells include solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma. In one preferred embodiment, the cancer is skin cancer.

Additional cancers that may serve as sources of cancer cells include blood borne cancer, such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

B. Method of Assessing a Risk of Progression of Skin Carcinoma in a Subject.

Another aspect of the invention provides a prognostic method to assess the risk of a skin SCC precursor to develop into SCC.

Prediction of a cellular or physiological characteristic includes the prediction of any cellular or physiological state that may be predicted by assessing the expression of a marker. Examples include the identity of a cell as a particular cell including a particular normal or cancer cell type, the likelihood that one or more diseases is present or absent, the likelihood that a present disease will progress, remain unchanged, or regress, the likelihood that a disease will respond or not respond to a particular therapy, or any other outcome. Further examples include the likelihood that a cell will move, senesce, apoptose, differentiate, metastasize, or change from any state to any other state or maintain its current state.

Expression of a marker in a sample may be more or less than that of a level predetermined to predict the presence or absence of a cellular or physiological characteristic. The expression of the marker in the sample may be more than 1,000,000×, 100,000×, 10,000×, 1000×, 100×, 10×, 5×, 2×, 1×, 0.5×, 0.1×0.01×, 0.001×, 0.0001×, 0.00001×, 0.000001×, 0.0000001× or less than that of a level predetermined to predict the presence or absence of a cellular or physiological characteristic.

The invention contemplates assessing the expression of the marker in any biological sample from which the expression may be assessed. One skilled in the art would know to select a particular biological sample and how to collect said sample depending upon the marker that is being assessed. Examples of sources of samples include but are not limited to biopsy or other in vivo or ex vivo analysis of prostate, breast, skin, muscle, fascia, brain, endometrium, lung, head and neck, pancreas, small intestine, blood, liver, testes, ovaries, colon, skin, stomach, esophagus, spleen, lymph node, bone marrow, kidney, placenta, or fetus. In some aspects of the invention, the sample comprises a fluid sample, such as peripheral blood, lymph fluid, ascites, serous fluid, pleural effusion, sputum, cerebrospinal fluid, amniotic fluid, lacrimal fluid, stool, or urine. Samples include single cells, whole organs or any fraction of a whole organ, in any condition including in vitro, ex vivo, in vivo, post-mortem, fresh, fixed, or frozen.

One type of cellular or physiological characteristic is the risk that a particular disease outcome will occur. Assessing this risk includes the performing of any type of test, assay, examination, result, readout, or interpretation that correlates with an increased or decreased probability that an individual has had, currently has, or will develop a particular disease, disorder, symptom, syndrome, or any condition related to health or bodily state. Examples of disease outcomes include, but need not be limited to survival, death, progression of existing disease, remission of existing disease, initiation of onset of a disease in an otherwise disease-free subject, or the continued lack of disease in a subject in which there has been a remission of disease. Assessing the risk of a particular disease encompasses diagnosis in which the type of disease afflicting a subject is determined. Assessing the risk of a disease outcome also encompasses the concept of prognosis. A prognosis may be any assessment of the risk of disease outcome in an individual in which a particular disease has been diagnosed. Assessing the risk further encompasses prediction of therapeutic response in which a treatment regimen is chosen based on the assessment. Assessing the risk also encompasses a prediction of overall survival after diagnosis.

Determining the level of expression that signifies a physiological or cellular characteristic may be assessed by any of a number of methods. The skilled artisan will understand that numerous methods may be used to select a level of expression for a particular marker or a plurality of markers that signifies particular physiological or cellular characteristics. In diagnosing the presence of a disease, a threshold value may be obtained by performing the assay method on samples obtained from a population of patients having a certain type of disease, for example, cancer, and from a second population of subjects that do not have the disease. In assessing disease outcome or the effect of treatment, a population of patients, all of which have a disease, such as cancer, may be followed for a period of time. After the period of time expires, the population may be divided into two or more groups. For example, the population may be divided into a first group of patients whose disease progresses to a particular endpoint and a second group of patients whose disease does not progress to the particular endpoint. Examples of endpoints include disease recurrence, death, metastasis or other states to which disease may progress. If expression of the marker in a sample is more similar to the predetermined expression of the marker in one group relative to the other group, the sample may be assigned a risk of having the same outcome as the patient group to which it is more similar.

In addition, one or more levels of expression of the marker may be selected that signify a particular physiological or cellular characteristic. For example, Receiver Operating Characteristic curves, or "ROC" curves, may be calculated by plotting the value of a variable versus its relative frequency in two populations. For any particular marker, a distribution of marker expression levels for subjects with and without a disease may overlap. This indicates that the test does not absolutely distinguish between the two populations with complete accuracy. The area of overlap indicates where the test cannot distinguish the two groups. A threshold is selected. Expression of the marker in the sample above the threshold indicates the sample is similar to one group and expression of the marker below the threshold indicates the sample is similar to the other group. The area under the ROC curve is a measure of the probability that the expression correctly indicated the similarity of the sample to the proper group. See, e.g., Hanley et al., *Radiology* 143: 29-36 (1982) hereby incorporated by reference.

Additionally, levels of expression for purpose of prognosis may be established by assessing the expression of a marker in a sample from one patient, assessing the expression of additional samples from the same patient obtained later in time, and comparing the expression of the marker from the later samples with the initial sample or samples. This method may be used in the case of markers that indicate, for example, progression or worsening of disease or lack of efficacy of a treatment regimen or remission of a disease or efficacy of a treatment regimen.

Other methods may be used to assess how accurately the expression of a marker signifies a particular physiological or cellular characteristic. Such methods include a positive likelihood ratio, negative likelihood ratio, odds ratio, and/or hazard ratio. In the case of a likelihood ratio, the likelihood that the expression of the marker would be found in a sample with a particular cellular or physiological characteristic is compared with the likelihood that the expression of the marker would be found in a sample lacking the particular cellular or physiological characteristic.

An odds ratio measures effect size and describes the amount of association or non-independence between two groups. An odds ratio is the ratio of the odds of a marker being expressed in one set of samples versus the odds of the marker being expressed in the other set of samples. An odds ratio of 1 indicates that the event or condition is equally likely to occur in both groups. An odds ratio greater or less than 1 indicates that expression of the marker is more likely to occur in one group or the other depending on how the odds ratio calculation was set up.

A hazard ratio may be calculated by estimate of relative risk. Relative risk is the chance that a particular event will take place. It is a ratio of the probability that an event such as development or progression of a disease will occur in samples that exceed a threshold level of expression of a marker over the probability that the event will occur in samples that do not exceed a threshold level of expression of a marker. Alternatively, a hazard ratio may be calculated by the limit of the number of events per unit time divided by the number at risk as the time interval decreases. In the case of a hazard ratio, a value of 1 indicates that the relative risk is equal in both the first and second groups. A value greater or less than 1 indicates that the risk is greater in one group or another, depending on the inputs into the calculation.

Additionally, multiple threshold levels of expression may be determined. This can be the case in so-called "tertile," "quartile," or "quintile" analyses. In these methods, multiple groups can be considered together as a single population, and are divided into 3 or more bins having equal numbers of individuals. The boundary between two of these "bins" may be considered threshold levels of expression indicating a particular level of risk of a disease developing or signifying a physiological or cellular state. A risk may be assigned based on which "bin" a test subject falls into.

C. A Method of Treating a Patient Having at Different Stage of Skin Squamous Cell Carcinoma.

Still another aspect of the present invention provides a method of treating a patient having skin squamous cell carcinoma or AK cells prone to progress into SCC. The method comprises testing one or more samples from the patient to determine the cell sensitivity to INPP5A metabolites. If a test is positive, i.e., the cells in the sample have reduced INPP5A expression on either mRNA or protein level, then treating the patient with pharmaceutical composition comprising at least one INPP5A metabolite. In one embodiment, INPP5A metabolite is selected from the group consisting of Ins(1,3,4)$P_3$, Ins(1,3,4,6)$P_4$, Ins(1,3,4,5,6)$P_5$, and Ins(1,2,3,4,5,6)$P_6$ (IP6). In one preferred example, the INPP5A metabolite is IP6. In one preferred embodiment, the pharmaceutical composition comprises IP6.

In general, the pharmaceutical composition will comprise an effective dosage amount of the disclosed one or more INPP5A metabolites, i.e., an amount of INPP5A metabolites sufficient to provide treatment to the subject being administered the pharmaceutical composition. Determination of an effective amount of the composition is within the capability of those skilled in the art. The effective amount of a pharmaceutical composition used to affect a particular purpose, as well as its toxicity, excretion, and overall tolerance may be determined in cell cultures or experimental animals by pharmaceutical and toxicological procedures either known now or by those skilled in the art or by any similar method yet to be disclosed. One example is the determination of the $IC_{50}$ (half maximal inhibitory concentration) of the pharmaceutical composition in vitro in cell lines or target molecules. Another example is the determination of the $LD_{50}$ (lethal dose causing death in 50% of the tested animals) of the pharmaceutical composition in experimental animals. The exact techniques used in determining an effective amount will depend on factors such as the type, physical and/or chemical properties of the pharmaceutical composition, the property being tested, and whether the test is to be performed in vitro or in vivo. The determination of an effective amount of a pharmaceutical composition will be well known to one of skill in the art who will use data obtained from any tests in making that determination. Determination of an effective amount of compound for addition to a cancer cell also includes the determination of an effective therapeutic amount, including the formulation of an effective dose range for use in vivo, including in humans.

In some embodiments, the pharmaceutical composition may comprise substantially pure INPP5A metabolite. In one preferred embodiment, the INPP5A metabolite is IP6 or a pharmaceutically acceptable salt thereof. The amount of INPP5A IP6 or a pharmaceutically acceptable salt thereof in such pharmaceutical compositions, therefore, may range from about 97%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, or about 3% by weight of the total amount of IP6 and its salt.

A variety of excipients commonly used in pharmaceutical formulations may be selected on the basis of several criteria, such as, the desired dosage form and the release profile properties of the dosage form. Non-limiting examples of suitable excipients include an agent selected from the group consisting of a binder, a filler, a non-effervescent disintegrant, an effervescent disintegrant, a preservative, a diluent, a flavoring agent, a sweetener, a lubricant, an oral dispersing agent, a coloring agent, a taste masking agent, a pH modifier, a stabilizer, a compaction agent, and combinations of any of these agents.

In one embodiment, the excipient may be a binder. Suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, peptides, and combinations thereof.

In another embodiment, the excipient may be a filler. Suitable fillers include carbohydrates, inorganic compounds, and polyvinylpirrolydone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, and sorbitol.

The excipient may be a non-effervescent disintegrant. Suitable examples of non-effervescent disintegrants include starches (such as corn starch, potato starch, and the like), pregelatinized and modified starches thereof, sweeteners, clays (such as bentonite), micro-crystalline cellulose, alginates, sodium starch glycolate, and gums (such as agar, guar, locust bean, karaya, pecitin, and tragacanth).

In another embodiment, the excipient may be an effervescent disintegrant. By way of non-limiting example, suitable effervescent disintegrants include sodium bicarbonate in combination with citric acid, and sodium bicarbonate in combination with tartaric acid.

The excipient may comprise a preservative. Suitable examples of preservatives include antioxidants (such as alpha-tocopherol or ascorbate) and antimicrobials (such as parabens, chlorobutanol or phenol). In other embodiments, an antioxidant such as butylated hydroxytoluene (BHT) or butylated hydroxyanisole (BHA) may be utilized.

In another embodiment, the excipient may include a diluent. Diluents suitable for use include pharmaceutically acceptable saccharides such as sucrose, dextrose, lactose, microcrystalline cellulose, fructose, xylitol, and sorbitol; polyhydric alcohols; starches; pre-manufactured direct compression diluents; and mixtures of any of the foregoing.

The excipient may include flavoring agents. Flavoring agents may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oils (such as lemon oil, orange oil, grape and grapefruit oil), and fruit essences (such as apple, peach, pear, strawberry, raspberry, cherry, plum, pineapple, and apricot).

In another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; stevia-derived sweeteners; chloro derivatives of sucrose such as sucralose; sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

In another embodiment, the excipient may be a lubricant. Suitable non-limiting examples of lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

The excipient may be a dispersion enhancer. Suitable dispersants may include starch, alginic acid, polyvinylpyrrolidones, guar gum, kaolin, bentonite, purified wood cellulose, sodium starch glycolate, isoamorphous silicate, and microcrystalline cellulose.

Depending upon the embodiment, it may be desirable to provide a coloring agent. Suitable color additives include food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in the present invention depending on the embodiment.

The excipient may include a taste-masking agent. Taste-masking materials include cellulose hydroxypropyl ethers (HPC); low-substituted hydroxypropyl ethers (L-HPC); cellulose hydroxypropyl methyl ethers (HPMC); methylcellulose polymers and mixtures thereof; polyvinyl alcohol (PVA); hydroxyethylcelluloses; carboxymethylcelluloses and salts thereof; polyvinyl alcohol and polyethylene glycol co-polymers; monoglycerides or triglycerides; polyethylene glycols; acrylic polymers; mixtures of acrylic polymers with cellulose ethers; cellulose acetate phthalate; and combinations thereof.

In various embodiments, the excipient may include a pH modifier. In certain embodiments, the pH modifier may include sodium carbonate or sodium bicarbonate.

The weight fraction of the excipient or combination of excipients in the pharmaceutical composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the pharmaceutical composition.

The pharmaceutical compositions detailed herein may be manufactured in one or several dosage forms. Suitable dosage forms include transdermal systems or patches. The transdermal system may be a matrix system, a reservoir system, or a system without rate-controlling membranes. Other suitable dosage forms also include tablets, including suspension tablets, chewable tablets, effervescent tablets or caplets; pills; powders such as a sterile packaged powder, a dispensable powder, and an effervescent powder; capsules including both soft or hard gelatin capsules such as HPMC capsules; lozenges; a sachet; a sprinkle; a reconstitutable powder or shake; a troche; pellets such as sublingual or buccal pellets; granules;

liquids for oral or parenteral administration; suspensions; emulsions; semisolids; or gels.

The dosage forms may be manufactured using conventional pharmacological techniques. Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., The Theory and Practice of Industrial Pharmacy (1986). Other methods include, e.g., prilling, spray drying, pan coating, melt granulation, granulation, wurster coating, tangential coating, top spraying, extruding, coacervation and the like.

The amount of active ingredient that is administered to a subject can and will vary depending upon a variety of factors such as the age and overall health of the subject, and the particular mode of administration. Those skilled in the art will appreciate that dosages may also be determined with guidance from Goodman & Goldman's The Pharmacological Basis of Therapeutics, Tenth Edition (2001), Appendix II, pp. 475-493, and the Physicians' Desk Reference. In one embodiment of the present invention, the effective amount of the disclosed compound to results in the slowing of expansion of the cancer cells would preferably result in a concentration at or near the target tissue that is effective in slowing cellular expansion in cancer cells, but have minimal effects on non-cancer cells, including non-cancer cells exposed to radiation or recognized chemotherapeutic chemical agents. Concentrations that produce these effects can be determined using, for example, apoptosis markers such as the apoptotic index and/or caspase activities either in vitro or in vivo. In one preferred embodiment, the effective dosage results in the resumed differentiation of SCC cell or its precursor AK cell, reduced cell proliferation of cancerous cell or its precursor and increased cancerous cell death.

Methods of administration include, but are not limited to, oral administration and parenteral administration. Parenteral administration includes, but is not limited to intradermal, intramuscular, intraperitoneal, intravenous, subcutaneous, intranasal, epidural, sublingual, intramsal, intracerebral, iratraventricular, intrathecal, intravaginal, transdermal, rectal, by inhalation, or topically to the ears, nose, eyes, or skin. Other methods of administration include but are not limited to infusion techniques including infusion or bolus injection, by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material.

Administration may be systemic or local. Local administration is administration of the disclosed compound to the area in need of treatment. Examples include local infusion during surgery; topical application, by local injection; by a catheter; by a suppository; or by an implant. Administration may be by direct injection at the site (or former site) of a cancer, tumor, or precancerous tissue or into the central nervous system by any suitable route, including intraventricular and intrathecal injection. Intraventricular injection can be facilitated by an intraventricular catheter, for example, attached to a reservoir, such as an Ommaya reservoir. Pulmonary administration may be achieved by any of a number of methods known in the art. Examples include use of an inhaler or nebulizer, formulation with an aerosolizing agent, or via perfusion in a fluorocarbon or synthetic pulmonary surfactant. The disclosed compound may be delivered in the context of a vesicle such as a liposome or any other natural or synthetic vesicle.

A pharmaceutical composition formulated so as to be administered by injection may be prepared by dissolving the disclosed compound with water so as to form a solution. In addition, a surfactant may be added to facilitate the formation of a homogeneous solution or suspension. Surfactants include any complex capable of non-covalent interaction with the disclosed compound so as to facilitate dissolution or homogeneous suspension of the compound.

Pharmaceutical compositions including the disclosed compound may be prepared in a form that facilitates topical or transdermal administration. Such preparations may be in the form of a liquid solution, cream, paste, lotion, shake lotion, powder, emulsion, ointment, gel base, transdermal patch or iontophoresis device. Examples of bases used in such compositions include petrolatum, lanolin, polyethylene glycols, beeswax, mineral oil, diluents such as water and alcohol, and emulsifiers and stabilizers, thickening agents, or any other suitable base now known or yet to be disclosed.

Addition of a pharmaceutical composition to cancer cells includes all actions by which an effect of the pharmaceutical composition on the cancer cell is realized. The type of addition chosen will depend upon whether the cancer cells are in vivo, ex vivo, or in vitro, the physical or chemical properties of the pharmaceutical composition, and the effect the composition is to have on the cancer cell. Nonlimiting examples of addition include addition of a solution including the pharmaceutical composition to tissue culture media in which in vitro cancer cells are growing; any method by which a pharmaceutical composition may be administered to an animal including intravenous, per os, parenteral, or any other of the methods of administration; or the activation or inhibition of cells that in turn have effects on the cancer cells such as immune cells (e.g. macophages and CD8+ T cells) or endothelial cells that may differentiate into blood vessel structures in the process of angiogenesis or vasculogenesis.

Treatment is contemplated in living entities including but not limited to mammals (particularly humans) as well as other mammals of economic or social importance, including those of an endangered status. Further examples include livestock or other animals generally bred for human consumption and domesticated companion animals. Treatment of a condition is the practice of any method, process, or procedure with the intent of halting, inhibiting, slowing or reversing the progression of a disease, disorder or condition, substantially ameliorating clinical symptoms of a disease disorder or condition, or substantially preventing the appearance of clinical symptoms of a disease, disorder or condition, up to and including returning the diseased entity to its condition prior to the development of the disease.

The method of treating a subject having a form of cancer includes the prevention of progression of the cancer to a neoplastic, malignant or metastatic state. Such preventative use is indicated in conditions known or suspected of preceding progression to cancer, in particular, where non- or pre-cancerous cell growth consisting of hyperplasia, metaplasia, or most particularly, dysplasia has occurred (for review of such abnormal growth conditions, see Robbins and Angell, 1976, *Basic Pathology*, 2d Ed., W. B. Saunders Co., Philadelphia, pp. 68-90, incorporated by reference). Hyperplasia is a form of controlled cell proliferation involving an increase in cell number in a tissue or organ, without significant alteration in structure or activity. For example, endometrial hyperplasia often precedes endometrial cancer and precancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism.

Alternatively or in addition to the presence of abnormal cell growth characterized as hyperplasia, metaplasia, or dysplasia, the presence of one or more characteristics of a transformed phenotype or of a malignant phenotype, displayed in vivo or displayed in vitro by a cell sample derived from a subject can indicate the desirability of prophylactic/therapeutic administration of the pharmaceutical composition that includes the compound. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. In a preferred embodiment, the characteristics of a transformed phenotype due to the treatment using pharmaceutical composition comprising INPP5A metabolite(s) is the differentiation of SCC cell or its precursor AK cell that leads to the cancerous cell death.

Pharmaceutical compositions that include the disclosed compound may be administered prior to, concurrently with, or after administration of a second pharmaceutical composition that may or may not include the compound. If the compositions are administered concurrently, they are administered within one minute of each other. If not administered concurrently, the second pharmaceutical composition may be administered a period of one or more minutes, hours, days, weeks, or months before or after the pharmaceutical composition that includes the compound Alternatively, a combination of pharmaceutical compositions may be cyclically administered. Cycling therapy involves the administration of one or more pharmaceutical compositions for a period of time, followed by the administration of one or more different pharmaceutical compositions for a period of time and repeating this sequential administration, in order to reduce the development of resistance to one or more of the compositions, to avoid or reduce the side effects of one or more of the compositions, and/or to improve the efficacy of the treatment.

The invention further encompasses methods of treating cancer that comprise combination therapies that comprise the administration of a pharmaceutical composition including the disclosed compound and another treatment modality. Such treatment modalities include but are not limited to, radiotherapy, chemotherapy, surgery, immunotherapy, cancer vaccines, radioimmunotherapy, treatment with pharmaceutical compositions other than those which include the disclosed compound, or any other method that effectively treats cancer in combination with the disclosed compound now known or yet to be disclosed. Combination therapies may act synergistically. That is, the combination of the two therapies is more effective than either therapy administered alone. This results in a situation in which lower dosages of both treatment modality may be used effectively. This in turn reduces the toxicity and side effects, if any, associated with the administration either modality without a reduction in efficacy.

In one preferred embodiment, the cancers or precancers that may be treated by pharmaceutical compositions including the disclosed compound either alone or in combination with another treatment modality is skin SCC.

(III) Kits.

The present invention further provides kits to be used in assessing the expression of a particular RNA in a sample from a subject to assess the risk of developing disease. Kits include any combination of components that facilitate the performance of an assay. A kit that facilitates assessing the expression of a RNA may include suitable nucleic acid-based and immunological reagents as well as suitable buffers, control reagents, and printed protocols.

Kits that facilitate nucleic acid based methods may further include one or more of the following: specific nucleic acids such as oligonucleotides, labeling reagents, enzymes including PCR amplification reagents such as Taq or Pfu; reverse transcriptase, or one or more other polymerases, and/or reagents that facilitate hybridization. Specific nucleic acids may include nucleic acids, polynucleotides, oligonucleotides (DNA, or RNA), or any combination of molecules that includes one or more of the above, or any other molecular entity capable of specific binding to a nucleic acid marker. In one aspect of the invention, the specific nucleic acid comprises one or more oligonucleotides capable of hybridizing to the marker.

A specific nucleic acid may include a label. A label may be any substance capable of aiding a machine, detector, sensor, device, or enhanced or unenhanced human eye from differentiating a sample that that displays positive expression from a sample that displays reduced expression. Examples of labels include but are not limited to: a radioactive isotope or chelate thereof, a dye (fluorescent or nonfluorescent), stain, enzyme, or nonradioactive metal. Specific examples include but are not limited to: fluorescein, biotin, digoxigenin, alkaline phosphatase, biotin, streptavidin, $^3$H, $^{14}$C, $^{32}$P, $^{35}$S, or any other compound capable of emitting radiation, rhodamine, 4-(4'-dimethylaminophenylazo) benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that signals the presence of the labeled nucleic acid. In one embodiment of the invention, the label includes one or more dyes optimized for use in genotyping. Examples of such dyes include but are not limited to: dR110, 5-FAM, 6FAM, dR6G, JOE, HEX, VIC, TET, dTAMRA, TAMRA, NED, dROX, PET, and LIZ.

An oligonucleotide is a reagent capable of binding a nucleic acid sequence. An oligonucleotide may be any polynucleotide of at least 2 nucleotides. Oligonucleotides may be less than 10, less than 15, less than 20, less than 30, less than 40, less than 50, less than 75, less than 100, less than 200, less than 500, or more than 500 nucleotides in length. While oligonucleotides are often linear, they may, depending on their sequence and conditions, assume a two- or three-dimensional structure. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. One skilled in the art would understand the length of oligonucleotide necessary to perform a particular task. Oligonucleotides may be directly labeled, used as primers in PCR or sequencing reactions, or bound directly to a solid substrate as in oligonucleotide arrays.

An oligonucleotide used to detect to an allele may be affixed to a solid substrate. Alternatively, the sample may be affixed to a solid substrate and the nucleic acid reagent placed into a mixture. For example, the nucleic acid reagent may be bound to a substrate in the case of an array or the sample may be bound to a substrate as the case of a Southern Blot, Northern blot or other method that affixes the sample to a substrate. A nucleic acid reagent or sample may be covalently bound to the substrate or it may be bound by some non covalent interaction including electrostatic, hydrophobic, hydrogen bonding, Van Der Waals, magnetic, or any other interaction by which an oligonucleotide may be attached to a substrate while maintaining its ability to recognize the allele to which it has specificity. A substrate may be any solid or semi solid material onto which a probe may be affixed, attached or printed, either singly or in the formation of a microarray. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any shape, including a spherical bead or flat surface. In some aspects of the invention, the probe may be affixed to a solid substrate. In other aspects of the invention, the sample may be affixed to a solid substrate.

Kits may also contain reagents that detect proteins, often through the use of an antibody. These kits will contain one or more specific antibodies, buffers, and other reagents configured to detect binding of the antibody to the specific epitope. One or more of the antibodies may be labeled with a fluorescent, enzymatic, magnetic, metallic, chemical, or other label that signifies and/or locates the presence of specifically bound antibody. The kit may also contain one or more secondary antibodies that specifically recognize epitopes on other antibodies. These secondary antibodies may also be labeled. The concept of a secondary antibody also encompasses non-antibody ligands that specifically bind an epitope or label of another antibody. For example, streptavidin or avidin may bind to biotin conjugated to another antibody. Such a kit may also contain enzymatic substrates that change color or some other property in the presence of an enzyme that is conjugated to one or more antibodies included in the kit.

A kit may also contain an indication of a result of the use of the kit that signifies a particular physiological or cellular characteristic. An indication includes any guide to a result that would signal the presence or absence of any physiological or cellular state that the kit is configured to predict. For example, the indication may be expressed numerically, expressed as a color or density of a color, expressed as an intensity of a band, derived from a standard curve, or expressed in comparison to a control. The indication may be communicated through the use of a writing. A writing may be any communication of the result in a tangible medium of expression. The writing may be contained physically in or on the kit (on a piece of paper for example), posted on the Internet, mailed to the user separately from the kit, or embedded in a software package. The writing may be in any medium that communicates how the result may be used to predict the cellular or physiological characteristic that the kit is intended to predict, such as a printed document, a photograph, sound, color, or any combination thereof.

The invention further encompasses pharmaceutical compositions that include the disclosed compound and/or pharmaceutically acceptable salts of the compound.

EXAMPLES

Various embodiments of the present teachings can be illustrated by the following non-limiting examples. The following examples are illustrative, and are not intended to limit the scope of the claims.

Methods and Material:

Tissues:

Tissue samples analyzed were formalin-fixed, paraffin-embedded (FFPE), archived specimens obtained under the Institutional Review Board—approved protocols at the Arizona Cancer Center, University of Arizona (Tucson, Ariz.); Southern Arizona Veterans Affairs Health Care System (Tucson, Ariz.); Loyola University Medical Center (Chicago, Ill.); and Mayo Clinic. The study was conducted according to the Declaration of Helsinki Principles.

Array CGH:

To obtain genomic DNA for aCGH (array-based comparative genomic hybridization), microscopic examination by pathologist was used to select the areas for harvest and DNA extraction. In all samples, only regions that showed >50% lesional content were harvested. aCGH profiling was done using a method in which DNA was extracted from FFPE tissue blocks using the DNeasy tissue kit (Qiagen, Germantown, Md.). Normal pooled lymphocyte DNA (Promega, Madison, Wis.) was used as a reference. A total of 5 µg of sample genomic DNA and 1 µg of reference genomic DNA were fragmented using the thermolabile recombinant shrimp DNase (TS-DNase; Affymetrix, Santa Clara, Calif.) to achieve an average DNA fragment length of 200 to 600 bp. Fragmented sample and reference DNA were labeled with Cy5 and Cy3 fluorescent dUTP, respectively, using the Bioprime Array CGH Genomic Labeling System (Invitrogen, Carlsbad, Calif.). Hybridizations were done on Agilent 44K feature microarrays for aCGH (Agilent Technologies, Santa Clara, Calif.) per the manufacturer's specifications and scanned on an Agilent DNA Microarray scanner, followed by image analysis with Feature Extraction software and data visualization with DNA Analytics software using the aberration calling algorithm ADM-1.

Fluorescence In Situ Hybridization:

Fluorescence in situ hybridization (FISH) was carried out using a centromeric probe to chromosome 10 (Abbott Molecular, Des Plaines, Ill.) and INPP5A-directed probes (bacterial artificial chromosomes RP11-500B2 and RP11-288G11; BACPAC Resource Center) to either metaphase spreads or sections prepared from FFPE blocks. The DNA from two large plasmids carrying a large segment of human chromosomal DNA in the INPP5A gene region (RP11-500B2 and RP11-288G11) was isolated and labeled with Cy5 tagged nucleotides, then hybridized to the FFPE slices from normal and SCC samples. FFPE slices were prepared for hybridization using the Paraffin Pretreatment Kit II (Abbott Molecular, Des Plaines, Ill.). Slides were examined and photographed on a Zeiss Axiophot equipped with interference filters (Chroma, Bellows Falls, Vt.) and a CoolSnap HQ2 digital camera (Photometrics, Tucson, Ariz.). The FISH evaluation was semi-quantitative. Whenever the tissue was of sufficient size, 100+ nuclei were examined. However, in cases where a lesion of interest was small (e.g., AK lesions), all available lesional nuclei (i.e., <100) were examined.

Immunohistochemistry:

FFPE tissue blocks were sectioned on glass slides at 5-µm thickness and baked for 60 minutes at 60° C. Slides were subsequently subjected to heat-induced epitope retrieval using a proprietary citrate-based retrieval solution for 20 minutes. The tissue sections were incubated for 30 minutes with anti-INPP5A mouse monoclonal antibody (clone 3D8; Novus Biologicals, Littleton, Colo.). The sections were visualized with the Bond Polymer Refine Detection kit (Leica Microsystems, Inc., Wetzlar, Germany) using diaminobenzidine chromogen as substrate.

IP6 Treatment of Squamous Cell Carcinoma:

The human head and neck squamous cell carcinoma lines evaluated were: SCC-4, SCC-9 and SCC-15. The colorectal cancer cell line HT-29 and the kidney embryonic line HEK293, purchased from the American Type Culture Collection (ATCC, Manassas, Va.), were used for comparison. Squamous cell lines were maintained in Dulbecco's Modified Eagle Medium: Nutrient Mixture F12 (DMEM/F12), with 10% Fetal bovine serum (FBS), 2 mM GlutaMAX, 25 mM Hepes buffer, 100 U/ml penicillin and 100 µg/ml streptomycin. HEK293 and HT-29 were cultured in DMEM and RPMI-1640 medium respectively, with the supplements mentioned above. All media and cell culture supplements were purchased from Invitrogen Corporation (Carlsbad, Calif.). Subconfluent, rapidly growing cells were plated at a density of 600 cells/20 µL/well in a clear bottom 384-well plate with opaque walls, suitable for luminescent measurements. The next day, IP6 (Inositol hexakisphosphate, phytic acid, dipotassium salt, Sigma-Aldrich, St Louis, Mo.) solutions in culture medium, corresponding to the following concentrations: 0.3125, 0.625, 1.25, 2.5 and 5 mM, were prepared, and were stored at 4° C. for 4-6 h. Shortly before treatment, IP6 solutions were centrifuged to remove any precipitates that IP6 forms with calcium chloride. Four wells were treated for each condition. 48 h after IP6 treatments, cells were assayed for viability using the CellTiter-Glo® Luminescent Cell Viability Assay kit, from PromegaBioSciences, Inc. (San Luis Obispo, Calif.), following the manufacturer's instruction. Briefly, the assay buffer and substrate were equilibrated at room temperature, and mixed thoroughly. Without removing medium from wells, the assay reagent was added into each well (1:1, volume:volume of medium per well) and the content was mixed for 2 minutes on an orbital shaker to induce cell lysis. The plate was incubated at room temperature for 10 minutes, and the luminescence was read on a Perkin Elmer Victor$^3$ microplate reader. Data from each set of four replicates was averaged and the standard deviation was calculated.

Statistics:

The two-tailed Fisher's exact test was used to compare the staining patterns between the cohorts of primary SCC tumors that have subsequently metastasized with those that have not. P values of <0.05 were considered statistically significant.

Example 1

The INPP5A Gene is Frequently Deleted in Cutaneous SCC Tumors

To identify novel genes and molecular mechanisms associated with cutaneous SCC (squamous cell carcinoma) development and progression, a series of archived skin tissues spanning a range from normal skin to invasive SCC were analyzed. An optimized high-resolution oligomer aCGH method was used on these archived FFPE tissues. This approach enabled detecting gene copy number changes with sensitivity and accuracy comparable with that obtained by analysis of DNA derived from frozen tissues.

aCGH was done using the DNA from a spectrum of 40 FFPE skin tissues, including normal skin (n=12), precancerous lesions of AK (n=5), in situ SCC lesions (SCCIS; n=2), and invasive SCCs (SCC; n=21). A total of 458 copy number aberrations were identified in the examined samples, 267 (58%) of which were amplifications and 191 (42%) were deletions. It was observed that there was an increase in the overall frequency of gene copy number aberrations per sample in proportion to the increasing malignant characteristics of the examined tissue, with invasive SCCs harboring, on average, the highest number of aberrations per genome (FIG. 1).

Figure 2:
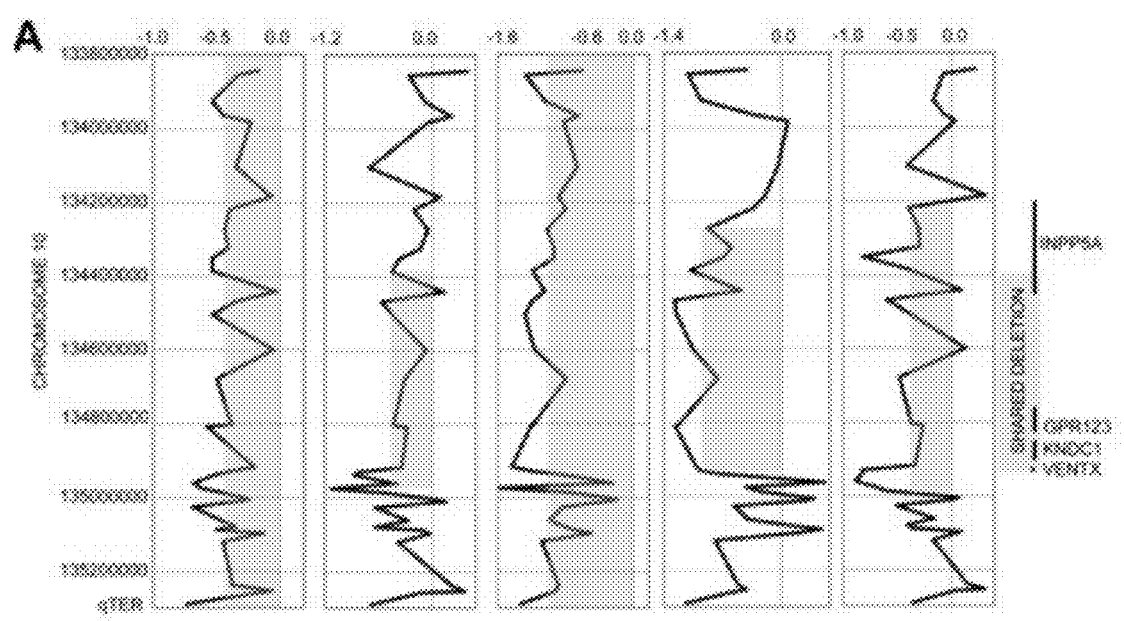
FIG. 2 depicts the identification of selected INPP5A deletions by aCGH.

Examination of the genomic regions characterized by recurrent copy number changes across samples, as detected by aCGH, identified a prevalent copy number aberration which was deletion of the q-ter region of chromosome 10, an area harboring the INPP5A (inositol polyphosphate 5-phosphatases) gene (FIG. 2). aCGH detected loss of the INPP5A gene in 1 of 2 examined SCCIS lesions, and in 5 of 21 (24%) examined invasive SCC tumors, but in none of the examined AK lesions or normal skin (Table 1).

TABLE 1

Frequency of INPP5A gene deletions as detected by CGH

| Tissue Type | Number with INPP5A deletion by aCGH |
|---|---|
| Normal | 0/12 |
| AK | 0/5 |
| SCCIS | 1/2 |
| SCC | 5/21 |

Figure 3:
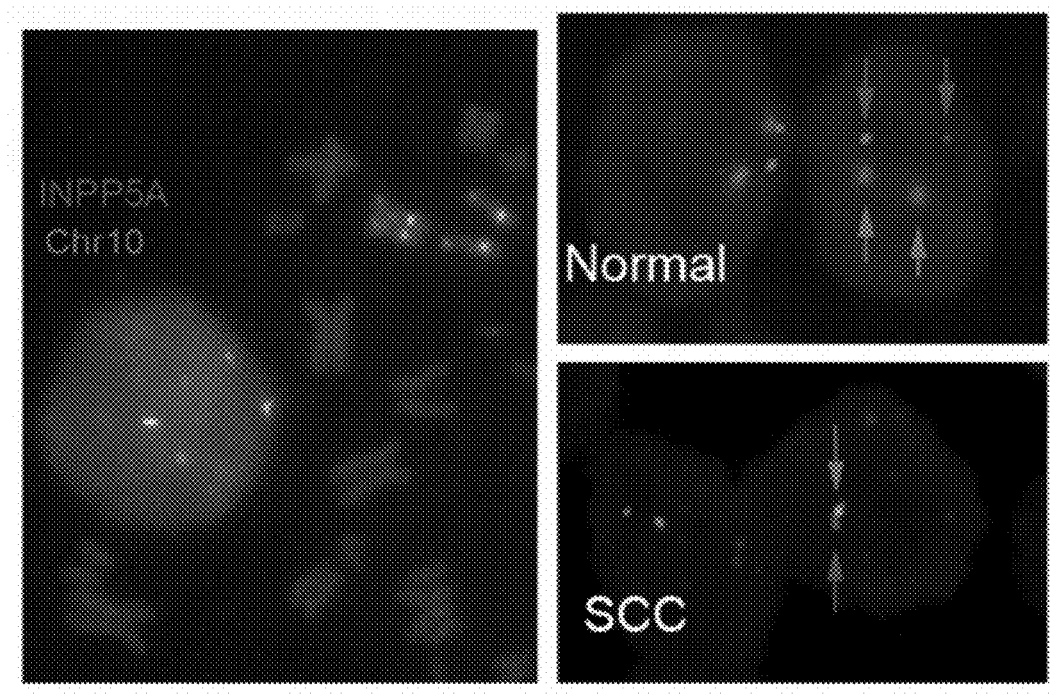
FIG. 3 depicts loss of INPP5A in a squamous cell carcinoma sample from a patient using blue fluorescence of DAPI bound to DNA (panel labeled as "SCC") to mark nuclei and chromosomes, green fluorescent probes to mark chromosome 10 centromeres, and red fluorescent probes to mark the INPP5A gene near the q-terminus of chromosome 10. A metaphase spread from normal cells is shown in panel labeled as "INPP5A Chr10". The presence of two copies of the chromosome 10 centromere and two copies of the INPP5A gene in normal skin cells from a patient is shown in panel labeled as "Normal". The presence of one copy of the chromosome 10 centromere and one copy of the INPP5A gene in SCC skin cells from the same patient is shown in panel labeled as "SCC"

To verify the accuracy of aCGH calls, FISH (fluorescent in situ hybridization) for INPP5A was performed in two of five samples that showed INPP5A deletions by aCGH. Both cases showed clear INPP5A loss, whereas control tissues showed no detectable loss of FISH signal (FIG. 3). Normal metaphase spread is provided as a reference, and two copies of INPP5A are seen in normal keratinocytes (FIG. 3, left and right-top panels) with INPP5A signal in red, but only one copy in SCC (FIG. 3, right-bottom panel).

The observed deletions of INPP5A in FIG. 3 represent a highly selected, nonrandom genetic event in SCC. Most of 191 deletions identified among SCC samples occur only once, whereas samples of a smaller proportion are observed as recurrent deletions, affecting more than one sample. The region of INPP5A is the single most frequently deleted segment in the interrogated SCC genomes, as well as the only recurrent deletion detected in five independent SCC samples. The core INPP5A deletion, characterized as the smallest area of overlap among the aberrations harboring INPP5A deletions (FIG. 2), covers a genetic segment containing 587,219 bp, of which 91,861 bp are in the INPP5A gene itself. In addition to INPP5A, this segment contains three other genes: GPR123, KNDC1, and VENTX. However, INPP5A is the only gene in this cluster repeatedly affected by the copy number transition (the edge of the aberration), being affected in three of five samples harboring deletion of this region. Taken together, therefore, INPP5A gene deletions are highly selected genetic events, rather than nonspecific bystander events in the context of the overall genomic instability of the SCC genome.

Example 2

INPP5A Protein Level is Frequently Reduced in Primary SCC Tissues

Genomic aberrations detected by aCGH, such as gene deletions, can indicate a "tip of the iceberg" phenomenon, where loss of a gene on the DNA level is seen in a subset of tumors, whereas in remaining cases the implicated gene may be deregulated by other mechanisms, including those affecting its mRNA and protein products, and thus the loss of a gene on the DNA level is not the only way by which loss of expressed protein can occur.

To evaluate whether the genetic loss of INPP5A observed with aCGH might be similarly indicative of a more general phenomenon of INPP5A loss in SCC, INPP5A protein levels were examined in an independent cohort of FFPE skin tissues by immunohistochemistry using a monoclonal antibody to INPP5A. A total of 71 archived SCC tumors were evaluated and compared with the matched normal skin from the same patient using the histologically normal epidermis, immediately adjacent to the SCC tumor as control. Stained slides were evaluated using a standard scoring system based on the intensity of staining (0-3), with score of 0 representing no staining and score of 3 as intense staining. If a relative difference in signal was observed between tissues being compared, it was recorded as a change in INPP5A protein level.

Figure 4:
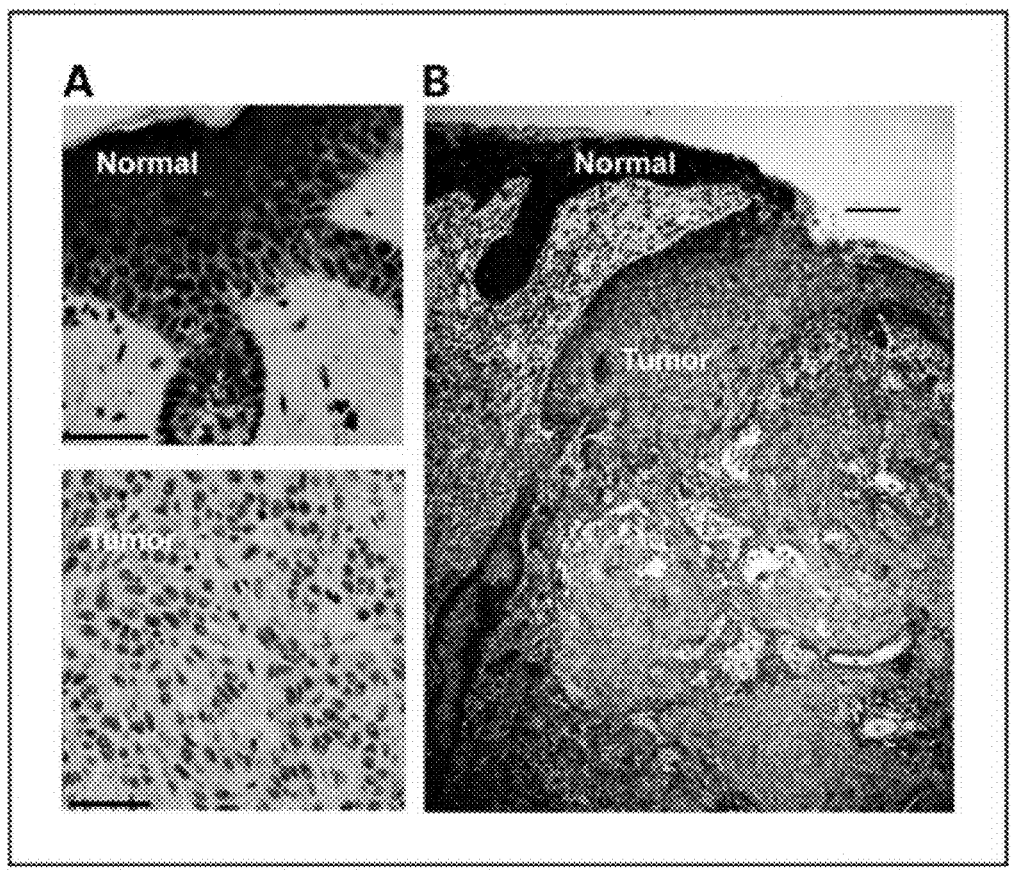
FIG. 4 depicts the detection of INPP5A protein loss in primary SCC tissues relative to the matched, normal epidermis. Immunohistochemistry for INPP5A was done on FFPE tissues, and relative intensity of INPP5A staining (dark brown) was compared between the SCC tissue and the adjacent, histologically normal epidermis. A, bottom, primary skin SCC tissue with low level of INPP5A staining; top, matched, adjacent normal epidermis from the same patient with dark staining in the dermal layer. B, a representative case is shown to further illustrate a relative difference in INPP5A staining between the primary SCC lesion and the adjacent normal epidermis. Scale bar, 50 µm.

Detection of INPP5A by immunohistochemistry showed mainly diffuse cytoplasmic signal. A comparison of INPP5A staining intensity between SCC tissues and matched normal epidermis identified three general staining patterns. The most prevalent pattern of expression, observed in 51 of 71 (72%) examined tissues, manifested as a relative reduction of INPP5A in SCC tissues when compared with matched normal skin (FIG. 4A). Only 20 of 71 (28%) examined tissues showed no difference in INPP5A staining between the SCC and matched normal skin. Importantly, no single case was observed where INPP5A staining was more intense in SCC tumor than in matched normal skin, further highlighting the specificity of the observed pattern (Table 2. A section; FIG. 4B). Notably, 10 SCC lesions examined in this cohort were classified by pathology as SCCIS (cutaneous squamous cell carcinomas in situ, a lesion with transepidermal keratinocyte atypia, indicating that the entire epidermis is filled with atypical keratinocytes). Six of 10 of these SCCIS lesions showed reduced INPP5A immunohistochemical signal, indicating no significant difference to the frequency detected in primary SCC in general. The observed reduction of INPP5A signal in SCC tissues is tumor specific, as the history of sun exposure and the extent of sun damage are comparable between the SCC lesion and the examined, adjacent normal epithelium used as a control. Since loss of INPP5A was shown to be present in a significant percentage of all stages of SCC, from precursor to metastatic disease, observing loss at AK, SCCIS, or local SCC indicates a risk that the lesion where the loss is observed in may continue to evolve through the stages to eventually become metastatic SCC. Taken together, a significantly higher frequency of INPP5A loss at the protein level compared with loss at the DNA level indicates that gene deletions may represent only one mechanism by which loss of INPP5A protein production can occur. There is also a sizable proportion of SCC tumors likely achieve the same effect through deregulation of INPP5A by other mechanisms to reduce the INPP5A protein level.

TABLE 2

Detection of INPP5A protein levels at successive stages of SCC progression

| INPP5A Staining Intensity | Frequency |
|---|---|
| A. Primary SCC compared to matched normal skin | |
| Normal skin > Primary SCC | 51/71 (72%) |
| Normal skin = Primary SCC | 20/71 (28%) |
| Normal skin < Primary SCC | 0/71 (0%) |
| B. AK compared to matched normal skin | |
| Normal skin > AK | 9/26 (35%) |
| Normal skin = AK | 17/26 (65%) |
| Normal skin < AK | 0/26 (0%) |
| C. Primary SCC compared to matched metastatic tissues | |
| Primary SCC > Met | 6/17 (35%) |
| Primary SCC = Met | 11/17 (65%) |
| Primary SCC < Met | 0/17 (0%) |

Example 3

INPP5A Loss on the Protein Level is an Early Event in SCC Development

To more precisely evaluate the timing of the reduction of INPP5A level in the development of cutaneous SCC, a series of 26 AKs (actinic keratoses, lesions in which atypical keratinocytes do no fill the epidermis) were examined, the earliest step in SCC development. Using immunohistochemistry, as described above, INPP5A protein levels between the AK lesions and adjacent normal epidermis were compared. A relative reduction of INPP5A in AK lesions was seen in 9 of 26 (35%) examined tissues, whereas 17 of 26 (65%) examined tissues showed no difference in INPP5A levels between the AK and normal epidermis (Table 2. B.).

To test whether the reduction of INPP5A protein in AKs is caused by genetic loss at the DNA level, such as seen in a subset of SCC tumors, FISH analysis was carried out, and no INPP5A gene deletion was detected in any of the examined cases. Although a small lesion size and limited number of lesional nuclei available for analysis in some of the studied AKs call for cautious interpretation of these results, it is important to note that no single lesion showed evidence of a clonal population with uniform loss of INPP5A FISH signal, even in cases where such clonal loss was suggested by immunohistochemical data. This absence of perturbations on DNA level in AKs may explain the relative paucity of gene copy number aberrations at early stages of disease detected by aCGH (FIG. 1) and indicates that deregulation of INPP5A expression in these precursor lesions occurs mainly at the mRNA or protein level.

Figure 5:
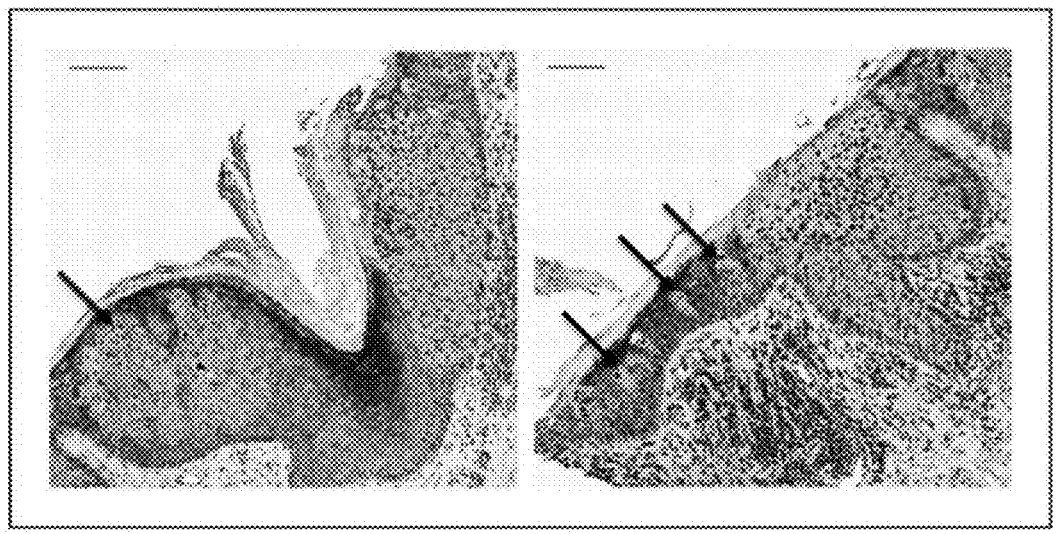
FIG. 5 depicts the detection of INPP5A loss in AK. Immunohistochemistry for INPP5A was done on FFPE tissues. Two representative lesions are shown in the left and right panel, each containing an area of SCCIS (evident by full epidermal thickness neoplasia; right half of each image), arising in association with an AK (partial epidermal thickness neoplastic change, consistent with AK; left half of each image). Arrows highlight populations of cells showing low level of INPP5A staining within the AK lesions. Scale bars, 100 µm.

The less frequent reduction of INPP5A protein levels in AK than in SCC lesions (35% versus 72%) is also informative and reflects a selection that favors progression of AK lesions with low INPP5A to the next stage of disease. FIG. 5 showed two representative lesions, each containing an area of SCCIS (evident by full epidermal thickness neoplasia; right half of each image), arising in association with an AK (partial epidermal thickness neoplastic change, consistent with AK; left half of each image). A pattern of INPP5A protein reduction in a subset of AKs, occurring in the form of strikingly demarcated regions of low INPP5A signal is an evidence for clonally expanding populations of affected cells within epidermis (FIGS. 5A and 5B). As SCCIS often arise within the preexisting lesions of AKs, this focal loss of INPP5A in AKs represents an early step toward a full oncogenic transformation along the spectrum of evolving epidermal neoplasia.

Example 4

Loss of INPP5A in Association with Progression to Metastatic Disease

The above data showed that deregulation of INPP5A levels as an early event in the development of keratinocyte neoplasia, provides a selective advantage in progression from AK to SCC. To assess a potential role of INPP5A loss in the process of tumor maintenance and progressions, the potential association of reduction of INPP5A level with the subsequent biological step in SCC progression and development of metastatic disease was tested. INPP5A protein levels were evaluated in a selected cohort of 17 patients with cutaneous SCC tumors that have subsequently metastasized, and INPP5A protein levels were also evaluated where both primary tumor tissue and matched regional metastatic tissue were available for examination. Immunohistochemical analysis of these paired tissues detected further reduction of INPP5A levels in the transition from primary to metastatic SCC in 6 of 17 (35%) examined tissue pairs (Table 2. C).

Although the remaining 11 of 17 (65%) studied pairs show no further loss of INPP5A levels in transition from primary to metastatic disease, there is no single case was identified where INPP5A staining was stronger in the metastatic tissue than in the primary SCC tumor. This observation further highlighted the specificity of the observed INPP5A loss in SCC progression. These data demonstrated that reduction of INPP5A levels, although an early event in development of SCC, also plays a role in progression of SCC from primary to metastatic disease in a significant subset of aggressive primary SCC tumors.

It was further noted during the INPP5A staining in the cohort of 17 patients with metastatic SCCs, there were normal epidermis present immediately adjacent to the primary SCC tissue in 13 of 17 examined primary SCCs. Twelve of 13 (92%) of these aggressive primary SCC tumors, which is a strikingly high frequency, showed loss of INPP5A staining when compared with the adjacent, normal epidermis. In comparison, in randomly selected primary SCC tumors, 51 of 71 (72%) SCC tumors showed reduction of INPP5A protein levels by immunohistochemistry (FIG. 4; Table 2A). Thus, higher frequency of INPP5A loss in primary SCC tumors that have shown an aggressive clinical course (i.e., subsequent development of metastases) indicates more aggressive primary disease. INPP5A level is, therefore, of prognostic value in assessing the risk of progression in primary SCC tumors.

Example 5

IP6 Reinitiates Terminal Differentiation of Cells with Reduced INPP5A Expression In normal skin, a gradient of increasing levels of INPP5A expression is seen as keratinocytes move from the basal proliferative layer and pass through the various non-proliferative differentiation stages that end at the cornified layer. In both AKs (actinic keratosis) and tumors, loss of INPP5A expression may represent an escape mechanism that inappropriately allows these cells to retain high proliferative capacity. Ectopic expression of INPP5A in SCC cell lines leads to apoptosis. INPP5A is known to play a role in the synthesis of inositol hexaphosphate (T6), and this compound exhibits effects on growth. Loss of INPP5A activity allows squamous cells to avoid cessation of growth and terminal differentiation. Exposure of cells that have lost INPP5A expression to IP6 reinitiates the terminal differentiation process. Specifically, exposure to IP6 induces apoptosis in SCC lines and primary, undifferentiated, proliferating keratinocytes in vitro. Therefore, the level of INPP5A expression identifies patients that would benefit from IP6 therapy.

Figure 6:
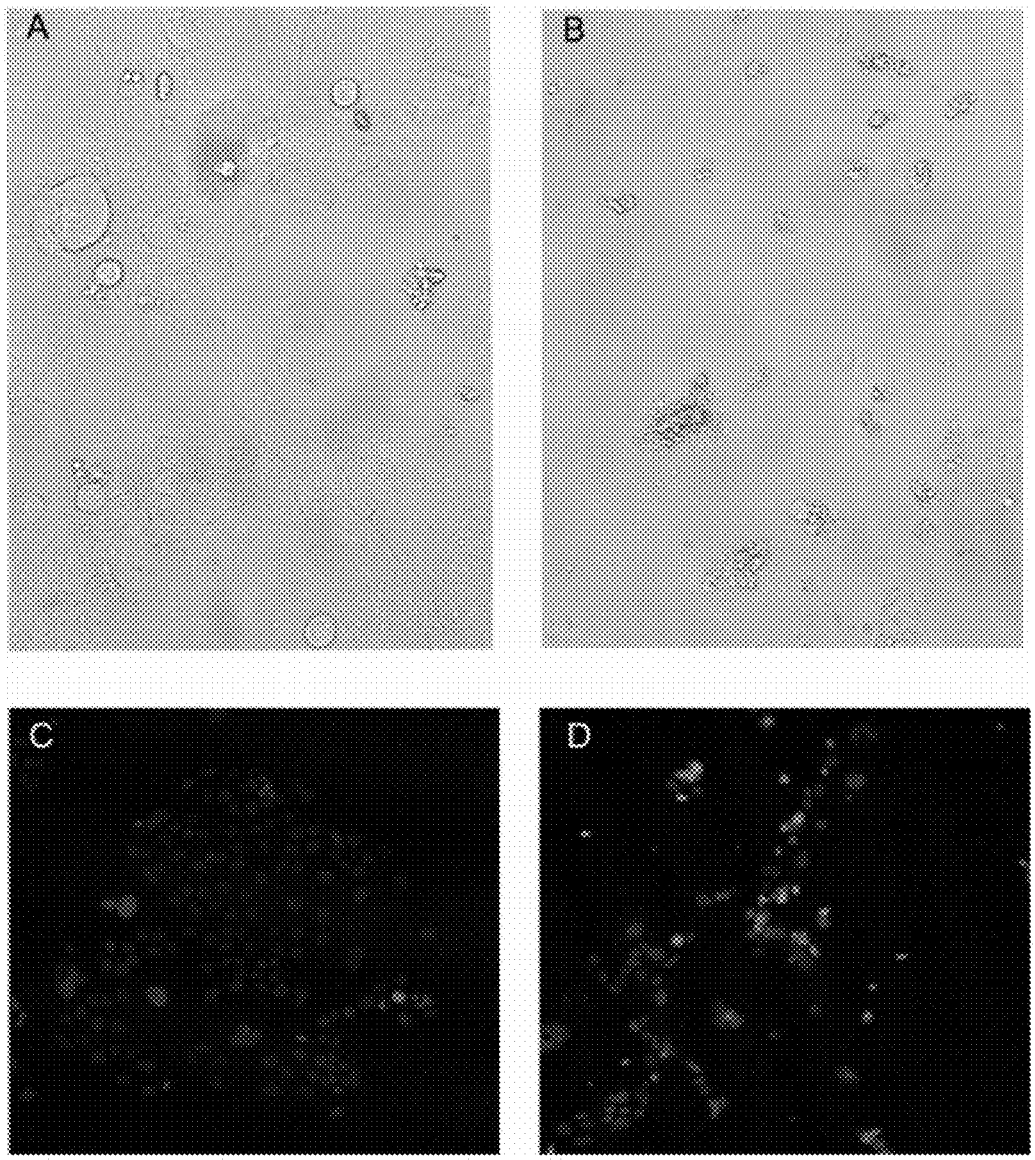
FIG. 6 depicts increased apoptosis in a squamous cell carcinoma cell line that carries a gene expression cassette that expresses INPP5A (B and D) compared to the same cell line carrying a gene expression cassette that expresses an unrelated protein, green fluorescent protein (A and C). DNA blue fluorescence in (C) and (D) was produced by DAPI probe, and apoptotic nuclei red fluorescence was produced through TUNEL assay.

SCC4 cells were infected with lentiviral vectors that delivered either CMV-GFP (control) or CMV-INPP5A. The cells were evaluated two weeks later. A 5-fold induction of INPP5A expression over baseline was confirmed by Quantitative Real-Time PCR. The q Real-Time PCR was done on an ABI PRISM® 7000 device using an ABI kit per the manufacturer's instructions (Applied Biosystems Carlsbad, Calif.). The primer pair used for detecting INPP5A m-RNA expression level were 5'-TTGCAGACTGTCCTTTGAC-3' (SEQ ID NO: 3) and 5'-AAACCCTTCTCGAATCGCTGA-3' (SEQ ID NO: 4). FIG. 6 depicts increased apoptosis in a squamous cell carcinoma cell line that carries a gene expression cassette that expresses INPP5A (B and D) compared to the same cell line carrying a gene expression cassette that expresses an unrelated protein, green fluorescent protein (A and C). The top panels of FIG. 6 depict CMV-GFP infected cells and CMV-INPP5A transfected cells in culture 2 weeks after infection (20×). The bottom panels show CMV-GFP and CMV-INPP5A infected SCC-4 cells after performance of TUNEL staining for cells undergoing apoptosis. Nuclei were stained blue using DAPI probe and apoptosis-positive cells are stained in red (lighter, more punctate). Overexpression of INPP5A results in significant cell death by apoptosis.

Figure 7:
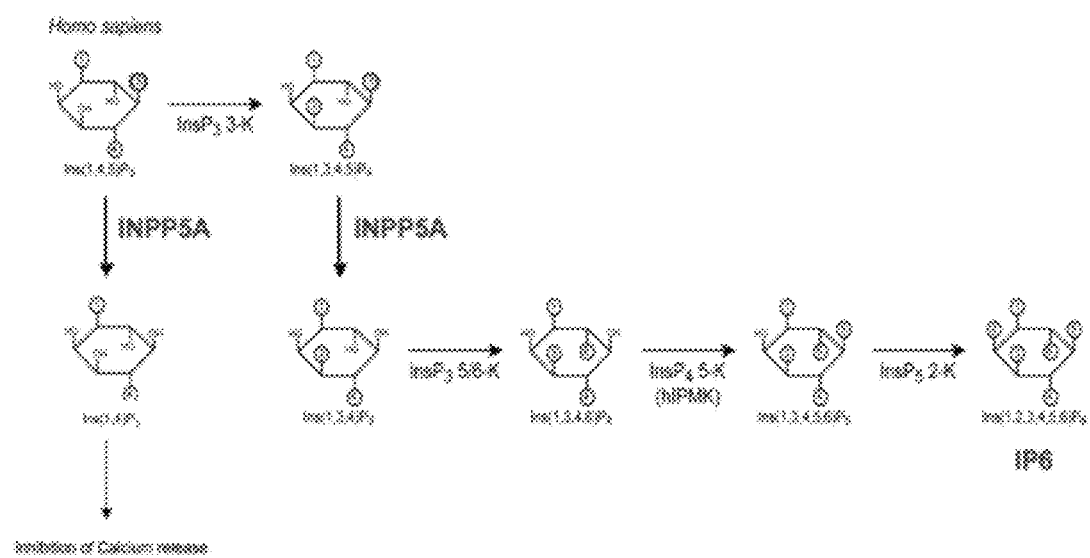
FIG. 7 depicts the biochemical pathway by which INPP5A directs the production of Ins(1,3,4)P3, which is subsequently converted to IP6.
Figure 8:
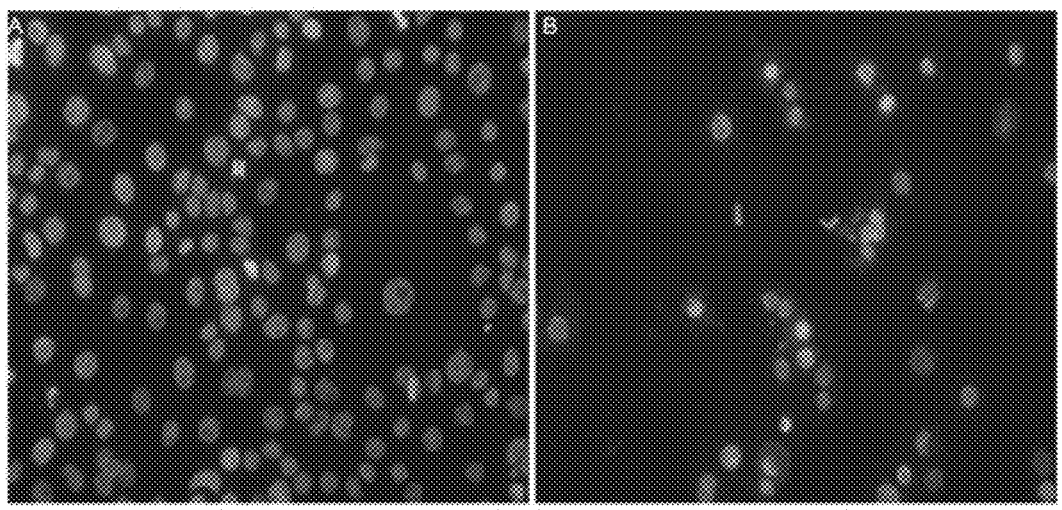
FIG. 8 depicts increased apoptosis in a squamous cell carcinoma cell line treated with IP6 (right panel B) relative to the same line without treatment (left panel A), and the DNA blue fluorescence was produced by DAPI probe. Apoptotic nuclei red fluorescence was produced through TUNEL assay.

IP6 is an inositol metabolite that is dependant upon INPP5A activity for its synthesis (See FIG. 7). Addition of exogenous IP6 inhibits the cell proliferation brought about by INPP5A loss and drives cells towards a differentiated phenotype. In FIG. 8, the left panel (A) shows untreated SCC-4 cells and the right panel (B) shows SCC-4 cells treated with IP6. Increased TUNEL staining (red) is seen in the IP6 treated cells. Therefore, treatment of SCC-4 cells with IP6 results in significant cell death by apoptosis, similar to the result seen in FIG. 8 with the overexpression of INPP5A.

Figure 9:
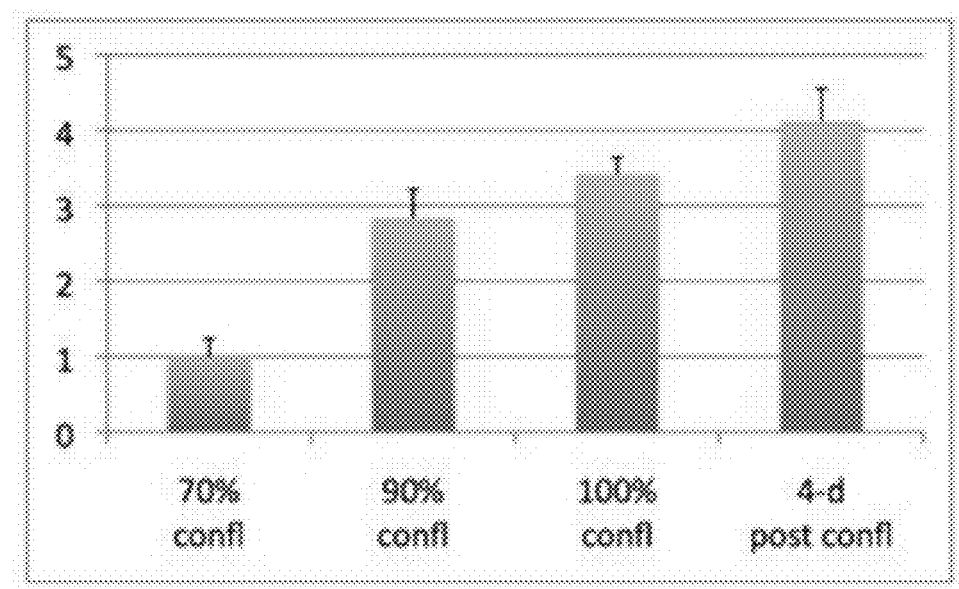
FIG. 9 depicts the fold change of INPP5A mRNA determined by q-RTPCR as a function of % confluence and differentiation of normal primary human keratinocytes.

IP6 is selective for cells with reduced INPP5A expression. Normal human keratinocytes were harvested at various stages of confluency. Cell cultures were assessed by morphological evaluation of the cell and segregated into distinct culture confluence intervals at or near the plateau phase of growth, generally: lower confluence (L), 70-80%; medium confluence (M), 80-90%, and higher confluence (H), >95%. INPP5A mRNA expression at selected culture confluence levels was evaluated by qPCR. INPP5A mRNA expression by q-RTPCR as a function of % of confluence of normal human keratinocytes are provided in Table 3 and FIG. 9.

TABLE 3

| INPP5A mRNA expression at selected confluence level | |
|---|---|
| Confluence | INPP5A mRNA Fold Change |
| 70% | 1 |
| 90% | 2.8 |
| 100% | 3.4 |
| 4-d post | 4.1 |

Figure 10:
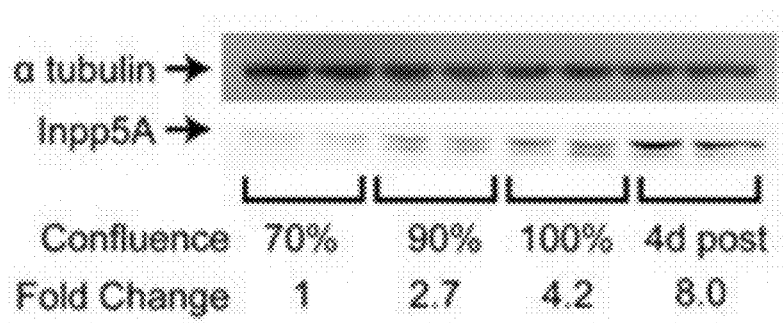
FIG. 10 depicts the change in INPP5A protein expression determined by Western blot as a function of the % confluence and differentiation of normal human keratinocytes.
Figure 11:
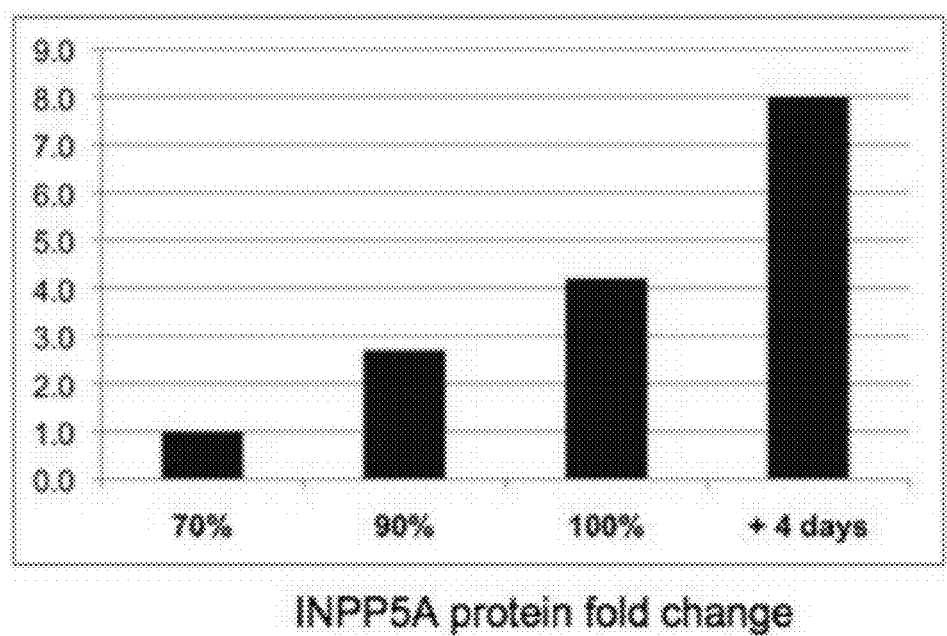
FIG. 11 depicts the data from FIG. 12 as a graph.

INPP5A protein level in cells at different confluence levels was measured using Western Blot (FIG. 10 and FIG. 11). Cytokeratin-10 (CK10) and integrin β4 are two known markers associated with keratinocyte differentiation. Keratinocyte differentiation level as a function of increased confluence was demonstrated by increased expression of Cytokeratin-10 (CK10) mRNA and decreased expression of integrin β4 mRNA as determined by qPCR using ABI TaqMan kits for detecting human KRT10 and human ITGB4 mRNA and provided in Table 4. These results are consistent with the expression patterns in keratinocyte differentiation.

TABLE 4

Expression of known markers of keratinocyte differentiation at selected confluence level

| NHK Confluence | Fold Induction mRNA | |
|---|---|---|
| | KRT10 | ITGB4 |
| 70% | 1.00 | 1.00 |
| 90% | 6.34 | 1.51 |
| 100% | 124.34 | 0.38 |
| 4-day post | 5294.22 | 0.66 |

Figure 12:
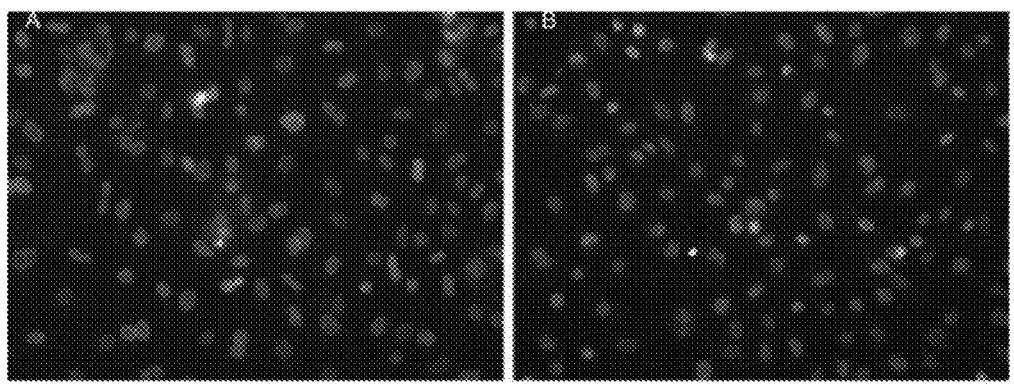
FIG. 12 depicts the effect of IP6 treatment on confluent normal human keratinocytes. Panel A shows confluent untreated normal human keratinocytes, while panel B shows confluent normal human keratinocytes treated with IP6. The DNA blue fluorescence was produced by DAPI probe. Apoptotic nuclei red fluorescence was produced through TUNEL assay.
Figure 13:
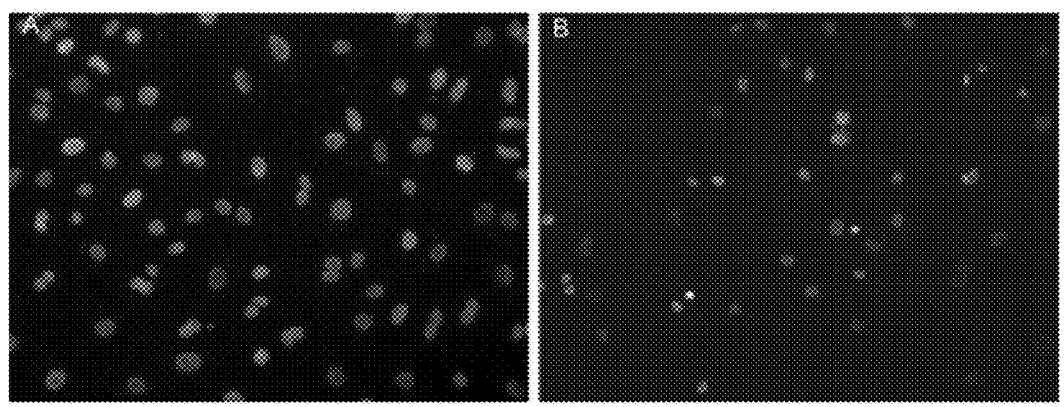
FIG. 13 depicts the effect of IP6 treatment on 70% confluent keratinocytes. Panel A shows untreated 70% confluent keratinocytes while panel B shows 70% confluent keratinocytes treated with IP6. The DNA blue fluorescence was produced by DAPI probe. Apoptotic nuclei red fluorescence was produced through TUNEL assay.

FIG. 12 and FIG. 13 depict reduced apoptosis in more highly confluent and differentiated keratinocytes. FIG. 12, left panel (A) shows 100% confluent keratinocytes that were untreated. and the right panel (B) shows 100% confluent keratinocytes treated with 2 mM IP6 for 24 hours. FIG. 13 left panel (A) shows 70% confluent keratinocytes that were untreated; and the right panel (D) shows 70% confluent keratinocytes that were treated with 2 mM IP-6 for 24 hours. Greater apoptosis relative to background was seen in the 70% confluent keratinocytes in comparison to the 100% confluent keratinocytes.

Example 6

INPP5A Cellular Characterization

Figure 14:
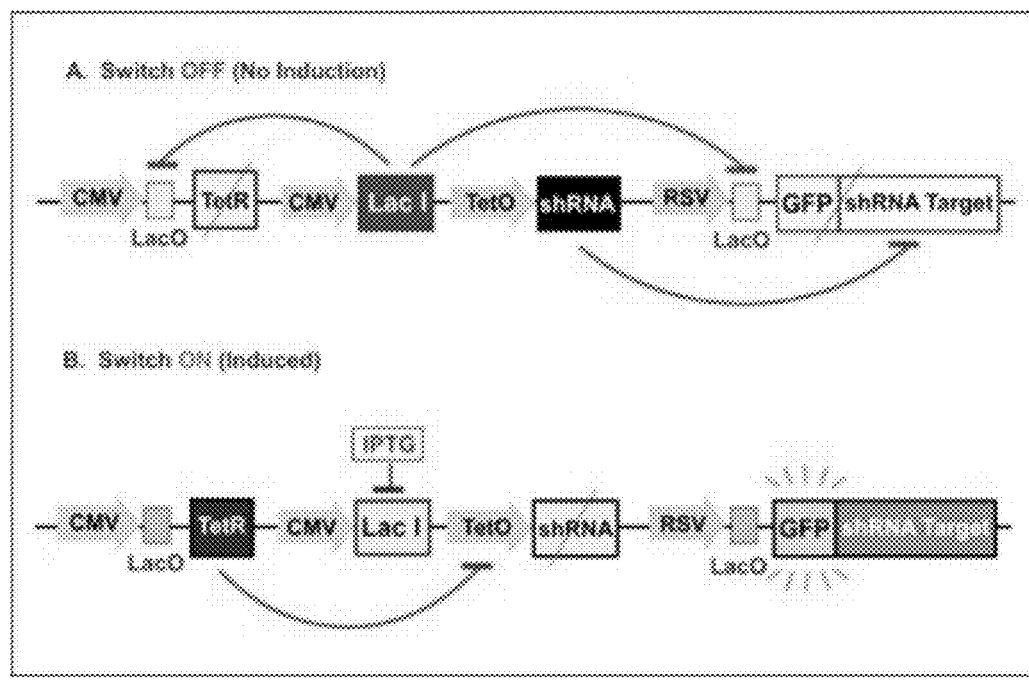
FIG. 14 depicts the plasmid composition of pTUNE vector used to deliver the INPP5A gene under controlled expression. The coding sequence for INPP5A replaces the GFP, shRNA Target region in the construct used to deliver the INPP5A. The schematic illustrations of the expression shut-down (A) and expression induction (B) are provided.
Figure 15:
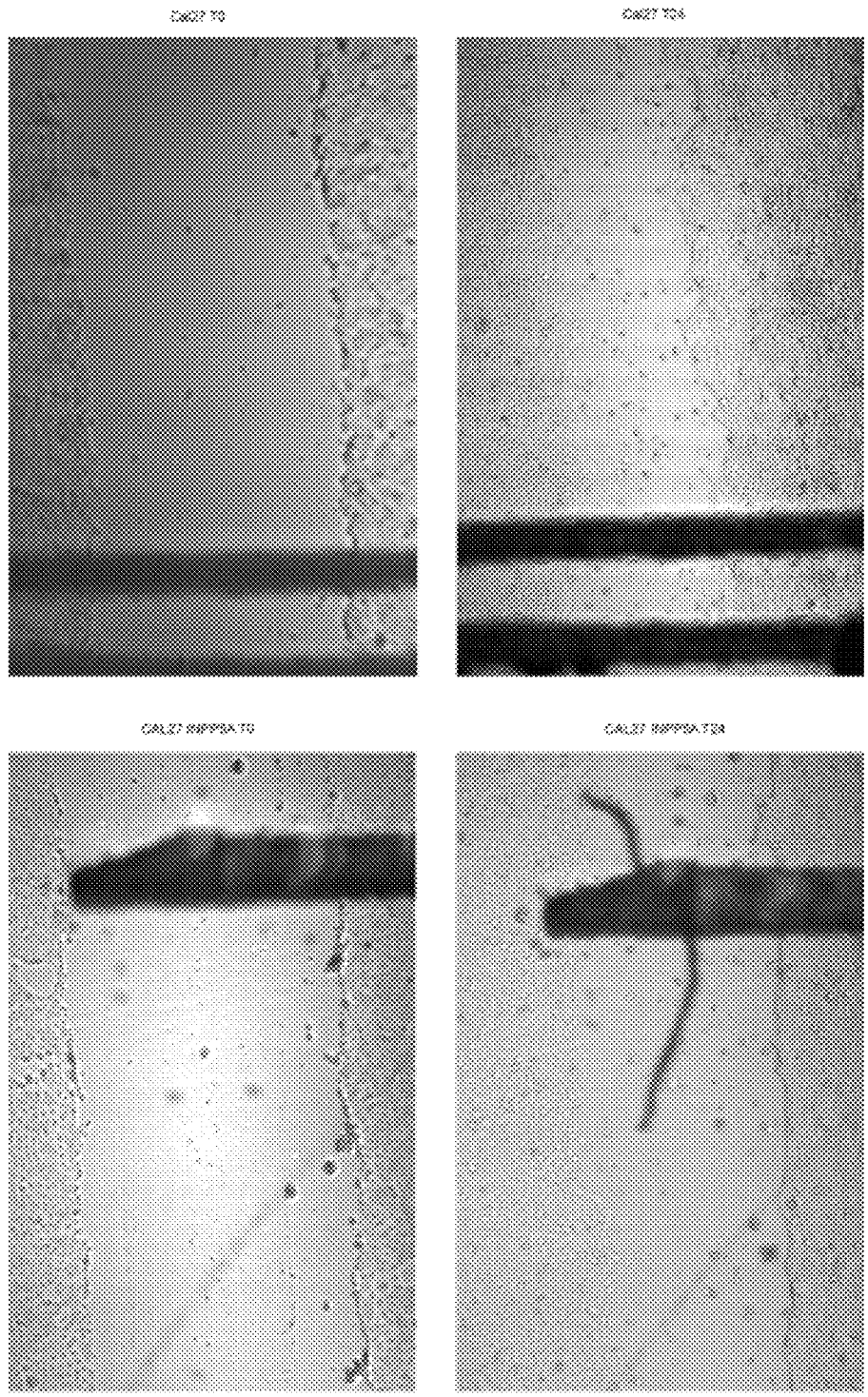
FIG. 15 depicts that before and after the introduction of controlled expression of INPP5A to cell line Cal-27, the production of a small amount of the protein was sufficient to reduce migration of cells in a scratch assay by 40%. A comparison of a 24 hour assay in the absence (top panels) or presence (bottom panels) of INPP5A in this cell line is shown.

INPP5A was delivered to cells in a controlled expression vector pTUNE, a derivative developed from a commercial vector (FIG. 14). Introduction of INPP5A with controlled expression allows production of a small amount of the protein. However, in the head and neck cancer cell line Cal27, the small amount of the INPP5A protein expression was sufficient to reduce migration in a scratch assay by 40%. A comparison of a 24-hour assay in the absence or presence of INPP5A in the Cal27 line is shown by the scratch assay shown in FIG. 15. While CAL27 did not show a growth reduction after INPP5A transfection, it did show a marked loss in motility (FIG. 15). A scratch assay shows fill-in of an approximately 1 mm scratch in 8 hours for the unmodified CAL27 line, but no fill in over 24 hours in the Cal-27+INPP5A transfectants. The growth rates of head and neck squamous cell carcinoma cell lines with and without the INPP5A expression plasmid were tested. Cell lines (Table 5) were plated in 12 well plates. Cal-27 and SCC-15 were grown in DMEM media, and SCC-9, -4, and -25 were grown in DMEM F12 media. All cell lines were grown to 70% confluence. 1.6 micrograms of AhdI linearized pTUNE INPP5A (Origene, Rockville, Md.) were transfected into the cell lines using lipofectamine and Optimem media (Invitrogen, Carlsbad, Calif.). After transfection, cells carrying the INPP5A bearing vector were selected with G418 at 1 microgram/ml for CAL27 and at 0.5 microgram/ml for the remaining cell lines. Cells were examined microscopically for outgrowth of transformants and those cell lines not growing were examined with the vital fluorescent stain Vybrant Violet (Invitrogen, Carlsbad, Calif.) to observe apoptotic nuclear decay. The results are provided in Table 5 below.

TABLE 5

Effects of INPP5A expression on growth of selected cell lines:

| Cell Line | Doubling time Control | Doubling Time + INPP5A | Comments |
|---|---|---|---|
| Cal-27 | 1-2 days | 1-2 days | no change |
| SCC-9 | 4-5 Days | 4-5 days | no change |
| SCC-15 | 2-3 days | NA | Slowly dying over 16 days post transfection (FIG. 18) |
| SCC-25 | 5-6 days | NA | Slowly dying over 12 days post transfection |
| SCC-4 | 4-5 days | NA | Cells all died within 4 days of transfection |

Figure 16:
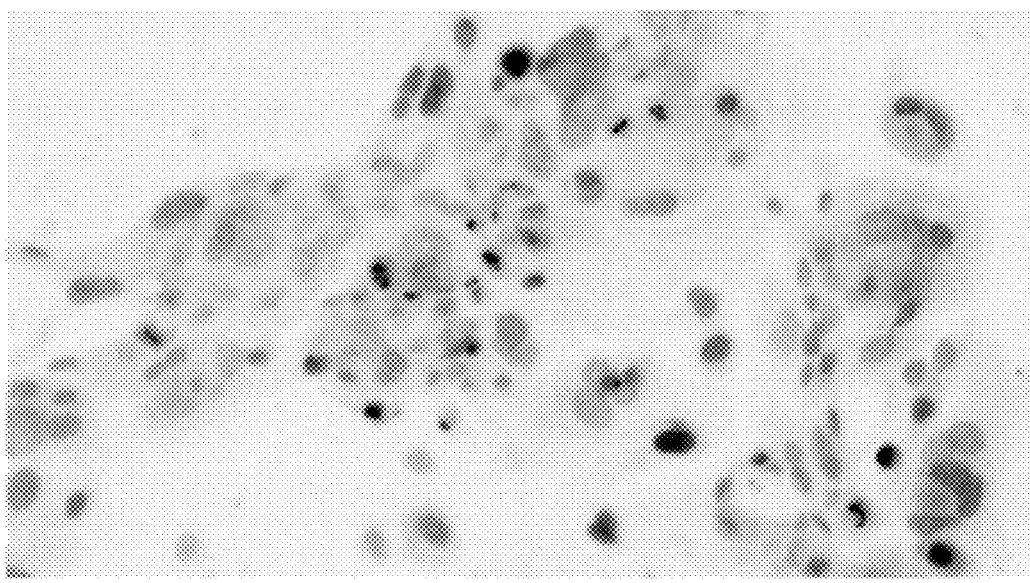
FIG. 16 depicts SCC 15 cells after the INPP5A pTUNE construct was delivered by transfection. The nuclei were stained with Vybrant Violet, producing fluorescence in live cells. Normal nuclei show as large, light gray bodies and apoptosing nuclei appear as small, dark, pycnotic nuclei.

Note that in SCC15+INPP5A and SCC-25+INPP5A, a vital nuclear dye shows pycnotic nuclei and apoptosis. FIG. 16 depicts SCC 15+INPP5A stained with Vybrant Violet, and the small, dark pycnotic nuclei were shown in apopotosis. Similar results were seen in SCC-25. Table 6 showed the q-Real-Time PCR results of INPP5A mRNA level in selected cell lines normalized to ACTB, a control gene. The primer used for INPP5A q-Real-Time PCR were 5'-TTGCAGACT-GTCCTTTGAC-3' (SEQ ID NO: 3) and 5'-AAACCCT-TCTCGAATCGCTGA-3' (SEQ ID NO: 4). The primers used for ACTB q-Real-Time PCR was 5'-TCATGAAGTGT-GACGTGGACATC-3' (SEQ ID NO: 5) and 5'-CAGGAG-GAGCAATGATCTTGATCT-3' (SEQ ID NO: 6).

TABLE 6 q-Real-Time PCR of INPP5A mRNA level in selected cell lines normalized to ACTB

| Cell Line | Critical Cycle INPP5A-ACTB | % of ACTB |
|---|---|---|
| CAL27 | 3.46 | 9.1% |
| CAL27 + INPP5A | 2.99 | 12.6% |
| SCC25 | 3.44 | 9.2% |
| SCC15 | 3.32 | 10.0% |
| SCC9 | 3.80 | 7.2% |
| SCC4 | 3.66 | 7.9% |

Example 7

Dose-Dependent IP6 Treatment of Squamous Cell Carcinoma

Figure 17:
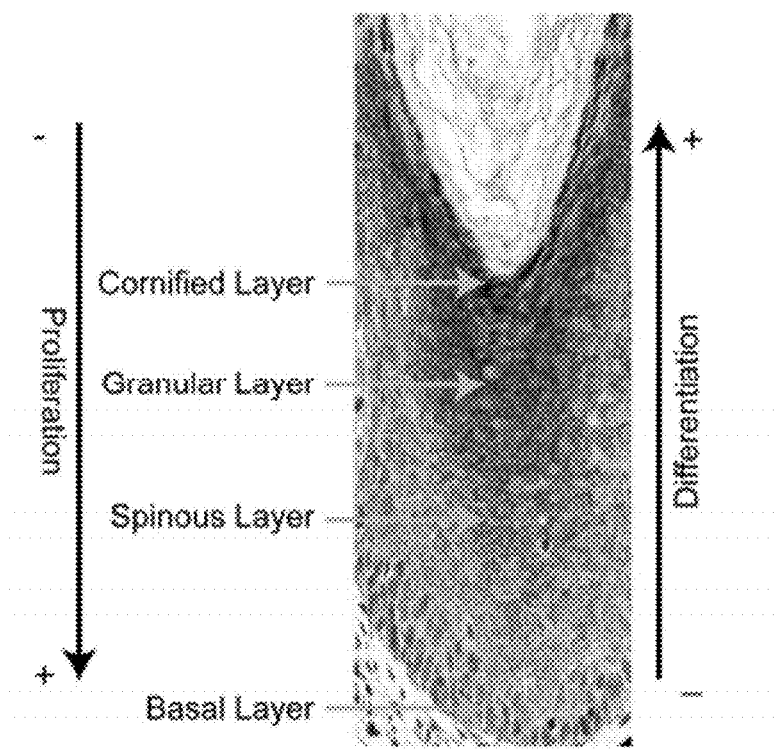
FIG. 17 depicts immunohistochemical staining for the presence of INPP5A which shows that it normally appears at a higher and higher level as keratinocytes go through the various stages of differentiation in the transition from actively growing precursor cells to the dead, cornified cells of the outer dermis.

The high frequency of loss of INPP5A in skin squamous cell carcinoma (SCC) and as well as its loss in sun damaged skin, an early precursor of SCC, was demonstrated in above examples. As shown in FIG. 5 and FIG. 17, immunohistochemical staining for the presence of INPP5A demonstrated that INPP5A normally appears at a higher and higher level as keratinocytes go through the various stages of differentiation in the transition from actively growing precursor cells to the dead, cornified cells of the outer dermis. Without being bound by theory, one way that INPP5A could be involved in this differentiation process is that it acts as a requisite enzyme in the formation of a small molecule involved in cell signaling. As INPP5A mediates the dephosphorylation of the 5 phospho group on either $Ins(1,4,5)P3$ or $Ins(1,3,4,5)P4$, the test in this example was carried out to determine whether restoring the phospho-inositol metabolites that are downstream of the INPP5A-mediated step to SCC cancer cell lines could lead to differentiation and death.

The diagram in FIG. 7 shows two inositol phosphate metabolic branches resulting directly from the action of INPP5A. In this invention, IP6 was tested for activity against a number of squamous cell cancer lines derived from head and neck tumors (SCC-4 SCC-15 SCC-9), and both a colorectal adenocarcinoma (HT-29) and a transformed normal human embryonic kidney cell line (HEK-293). Cultures of 600 cells for each of these lines in growth media were established in wells of a 384 well plate, and then sets of four replicates per dose were treated by the addition of no drug, 0.31 mM, 0.63 mM, 1.25 mM, 2.5 mM and 5 mM IP6. These treated and untreated cultures were allowed to grow for 72 hours in a tissue culture incubator and then were treated with and equal volume of Cell Titer Glow reagent, which lyses the cells and produces light through a reaction utilizing the ATP available from the cells.

Figure 18:
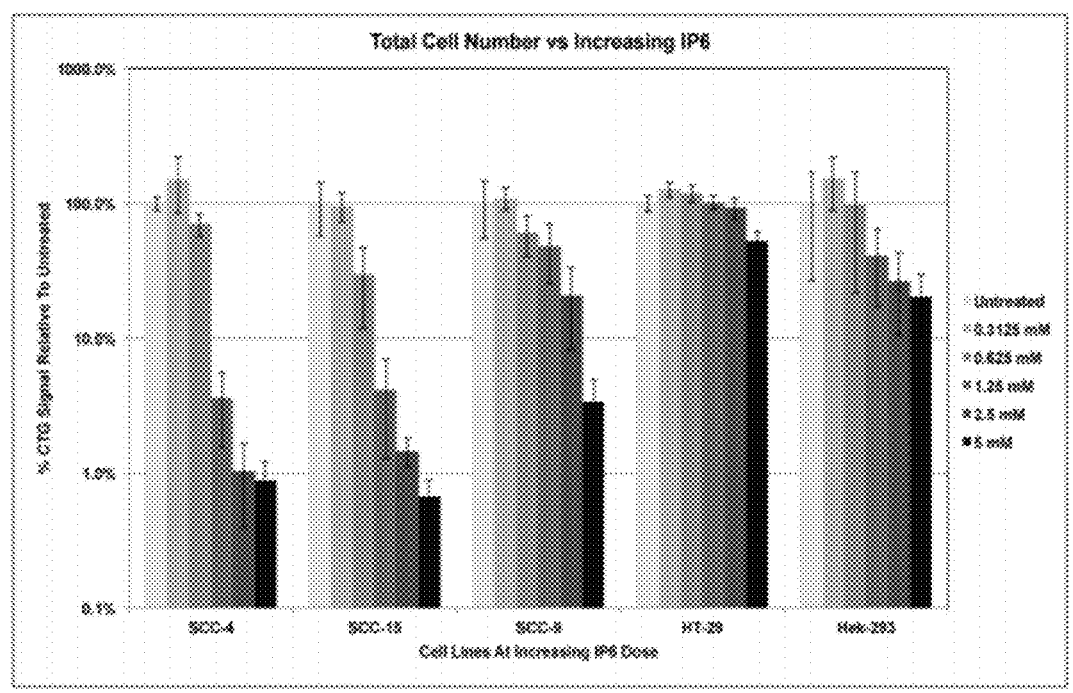
FIG. 18 depicts IP6 activity against a number of squamous cell cancer lines SCC-4 SCC-15 SCC-9, and both a colorectal adenocarcinoma (HT-29) and a transformed normal human embryonic kidney cell line (HEK-293). The cells showed a dose dependent reduction in number suggesting that effects due to INPP5A's loss can to some extent be corrected by supplying IP6 whose synthesis normally requires the activity of INPP5A.

The proportion of cells present after treatment relative to the number of cells in the unteated cells was shown in FIG. 18.

As demonstrated, the cells showed a dose-dependent reduction in number, which is much greater for the SCC cells than for the colorectal adenocarcinoma or the transformed human embryonic kidney cells. This data presented that INPP5A's loss leads to a failure of cells produced by less differentiated basal cells to cease proliferating and differentiate to from a liner layer and that this loss of regulation can to some extent be corrected by supplying an inositol phosphate metabolite whose synthesis normally requires the activity of INPP5A. Therefore the detection of loss of INPP5A activity in tumors that are dependent on this loss for their survival will prove useful in directing therapy for these tumors.

We claim:

1. A method of treating a subject having skin squamous cell carcinoma, the method comprising the steps of:
   testing the subject for tumor cells with reduced activity in the inositol polyphosphate5-phosphatase (INPP5A) pathway in comparison to a control in order to determine that the tumor cells are sensitive to a pharmaceutical composition comprising inositol hexaphosphate (IP6) and pharmaceutically acceptable salts thereof, wherein testing the subject for tumor cells with reduced activity in the INPP5A pathway consists of detecting the gene expression of INPP5A by hybridization with an oligonucleotide complementary to a portion of SEQ ID NO:1 or detecting the protein expression of INPP5A with an antibody that binds to a portion of SEQ ID NO:2; and
   administering an effective amount of the pharmaceutical composition to the subject when the subject is determined to have tumor cells that are sensitive to the pharmaceutical composition.

2. The method of claim 1, wherein testing the subject for tumor cells with reduced activity in the INPP5A pathway in order to determine that the tumor cells are sensitive to a pharmaceutical composition further comprises receiving a sample from the subject.

3. The method of claim 1, wherein the control is selected from the group consisting of normal skin tissue, normal skin adjacent to the tumor of the same subject, skin tissue from a less progressed tumor including actinic keratosis and squamous cell carcinoma in situ of the same subject.

4. The method of claim 1, wherein the administering an effective amount of the pharmaceutical composition to the subject is selected from the group consisting of oral administration, topical administration, and parenteral administration.

5. The method of claim 2, wherein the sample comprises a skin sample.

6. The method of claim 2, wherein the sample comprises a cell selected from the group consisting of an actinic keratosis cell, a squamous cell carcinoma in situ cell, a squamous cell carcinoma cell, and a metastatic squamous cell carcinoma cell.

7. The method of claim 1, wherein reduced activity in the INPP5A pathway is determined to be caused by deletion of at least one copy of INPP5A at chromosome 10q26.3.

* * * * *